US008569465B2

(12) United States Patent
Ralph et al.

(10) Patent No.: US 8,569,465 B2
(45) Date of Patent: Oct. 29, 2013

(54) METHOD FOR MODIFYING LIGNIN STRUCTURE USING MONOLIGNOL FERULATE CONJUGATES

(75) Inventors: John Ralph, Madison, WI (US); John H. Grabber, Mazomanie, WI (US); Ronald D. Hatfield, Madison, WI (US); Fachuang Lu, Madison, WI (US)

(73) Assignees: Wisconsin Alumni Research Foundation, Madison, WI (US); The United States of America, as represented by the Secretary of Agriculture, Washington, DC (US)

( * ) Notice: Subject to any disclaimer, the term of this patent is extended or adjusted under 35 U.S.C. 154(b) by 249 days.

(21) Appl. No.: 12/830,905

(22) Filed: Jul. 6, 2010

(65) Prior Publication Data

US 2011/0003978 A1 Jan. 6, 2011

Related U.S. Application Data

(60) Provisional application No. 61/213,706, filed on Jul. 6, 2009.

(51) Int. Cl.
*C07G 1/00* (2011.01)
*C08H 7/00* (2011.01)
*C08L 97/00* (2006.01)

(52) U.S. Cl.
USPC .......................................................... 530/500

(58) Field of Classification Search
USPC .......................................................... 530/500
See application file for complete search history.

(56) References Cited

U.S. PATENT DOCUMENTS

| 4,107,111 | A  | * | 8/1978 | Lindberg et al. | 524/735 |
| 4,478,747 | A  | * | 10/1984 | Crawford et al. | 435/72 |
| 5,451,514 | A  | * | 9/1995 | Boudet et al. | 800/286 |
| 5,824,842 | A  | * | 10/1998 | MacKay et al. | 800/260 |
| 6,455,762 | B1 | * | 9/2002 | Chiang et al. | 800/298 |
| 7,317,136 | B1 | * | 1/2008 | Forster et al. | 800/278 |
| 7,413,882 | B2 | * | 8/2008 | Berka et al. | 435/105 |
| 7,435,556 | B2 | * | 10/2008 | Viitanen et al. | 435/15 |
| 7,604,968 | B2 | * | 10/2009 | Schmidt-Dannert et al. | 435/183 |
| 7,981,650 | B2 | * | 7/2011 | Levasseur et al. | 435/183 |
| 2001/0007762 | A1 | * | 7/2001 | Echigo et al. | 435/128 |
| 2003/0070192 | A1 | * | 4/2003 | Keller et al. | 800/287 |
| 2003/0167511 | A1 | * | 9/2003 | Narbad et al. | 800/278 |
| 2003/0216326 | A1 | * | 11/2003 | Alimi | 514/22 |
| 2003/0226168 | A1 | * | 12/2003 | Carlson | 800/279 |
| 2004/0049802 | A1 | * | 3/2004 | Dixon et al. | 800/278 |
| 2004/0058983 | A1 | * | 3/2004 | Vuorela et al. | 514/456 |
| 2006/0005270 | A1 | * | 1/2006 | Dunn-Coleman et al. | 800/278 |
| 2006/0183895 | A1 | * | 8/2006 | Bloksberg et al. | 536/23.6 |
| 2008/0032344 | A1 | * | 2/2008 | Fallavollita | 435/72 |

(Continued)

OTHER PUBLICATIONS

Nakamura et al. (Cellulose Chem. Technol. 12, 209-221, 1978).*

(Continued)

*Primary Examiner* — Liam Heincer
(74) *Attorney, Agent, or Firm* — Joseph T. Leone, Esq.; Daniel A. Blasiole; DeWitt Ross & Stevens, S.C.

(57) ABSTRACT

Described is an isolated lignified plant cell wall including lignin, wherein the lignin includes a ferulate residue incorporated therein, such as from coniferyl ferulate and/or sinapyl ferulate. Also described is a method to make the isolated lignified plant cell wall, and the lignin produced by the method.

24 Claims, 11 Drawing Sheets

(56) References Cited

U.S. PATENT DOCUMENTS

| | | | | |
|---|---|---|---|---|
| 2009/0044294 | A1* | 2/2009 | Dixon et al. | 800/278 |
| 2009/0209739 | A1* | 8/2009 | Funaoka et al. | 530/502 |
| 2010/0058498 | A1* | 3/2010 | Apuya et al. | 800/298 |
| 2010/0178670 | A1* | 7/2010 | Smith et al. | 435/41 |
| 2010/0287660 | A1* | 11/2010 | Spangenberg et al. | 800/278 |
| 2010/0305244 | A1* | 12/2010 | Balakshin et al. | 524/76 |

OTHER PUBLICATIONS

Donaldson (Phytochemistry 57 (2001) 859-873).*
Howard et al., African Journal of Biotechnology vol. 2(12), 602-619, 2003.*
Baucher et al., Lignin: Genetic Engineering and Impact on Pulping, *Crit. Rev. Biochem. Mol. Biol.* 2003, 38, 305-350.
Blumenkrantz et al., New Method for Quantitative Determination of Uronic Acids, *Anal. Biochem.* 1973, 54, 484-489.
Dien et al., Converting Herbaceous Energy Crops to Bioethanol: A Review with Emphasis on Pretreatment Processes, *Handbook of Industrial Biocatalysis*; CRC Press LLC: Boca Raton, FL, 2005; pp. 1-11.
Dien et al., Chemical composition and response to dilute-acid pretreatment and enzymatic saccharification of alfalfa, reed canarygrass, and switchgrass, *Biomass Bioenergy* 2006, 30, 880-891.
Fahey et al., In *Forage Cell Wall Structure and Digestibility*; Jung, H. G., Buxton, D. R., Hatfield, R. D., Ralph, J., Eds.; Am. Soc. Agronomy: Madison, WI, 1993; pp. 715-766.
Fukushima et al., Comparison of the Acetyl Bromide Spectrophotometric Method with Other Analytical Lignin Methods for Determining Lignin Concentration in Forage Samples, *J. Agric. Food Chem.* 2004, 52, 3713-3720.
Grabber et al., Ferulate Cross-Linking in Cell Walls Isolated From Maize Cell Suspensions, *Phytochemistry* 1995, 40, 1077-1082.
Grabber et al., Dehydrogenation Polymer—Cell Wall Complexes as a Model for Lignified Grass Walls, *J. Agric. Food Chem.* 1996, 44, 1453-1459.
Grabber et al., p-Coumaroylated Syringyl Units in Maize Lignin: Implications for β-Ether Cleavage by Thioacidolysis, *Phytochemistry* 1996, 43, 1189-1194.
Grabber et al., Ferulate Cross-Links Limit the Enzymatic Degradation of Synthetically Lignified Primary Walls of Maize, *J. Agric. Food Chem.* 1998, 46, 2609-2614.
Grabber et al., Cross-Linking of Maize Walls by Ferulate Dimerization and Incorporation into Lignin, *J. Agric Food. Chem.* 2000, 48, 6106-6113.
Grabber et al., Model Studies of Ferulate-Coniferyl Alcohol Cross-Product Formation in Primary Maize Walls: Implications for Lignification in Grasses, *J. Agric. Food Chem.* 2002, 50, 6008-6016.
Grabber et al., Apoplastic pH and Monolignol Addition Rate Effects on Lignin Formation and Cell Wall Degradability in Maize, *J. Agric. Food Chem.* 2003, 51, 4984-4989.
Grabber, J. H., How Do Lignin Composition, Structure, and Cross-Linking Affect Degradablity? A Review of Cell Wall Model Studies, *Crop Sci.* 2005, 45, 820-831.
Grabber et al., Formation of syringyl-rich lignins in maize as influenced by feruloylated xylans and p-coumaroylated monolignols, *Planta* 2007, 226, 741-751.
Gratzl et al., L. *Lignin: Historical, Biological, and Materials Perspectives*; ACS Symposium Series; American Chemical Society: Washington, DC, 2000; vol. 742, pp. 392-421.
Hartley et al., Monomeric and Dimeric Phenolic Acids Released from Cell Walls of Grasses by Sequential Treatment with Sodium Hydroxide, *J. Sci. Food Agric.* 1991, 55, 365-375.

Hatfield et al., A Comparison of the Insoluble Residues Produced by the Klason Lignin and Acid Detergent Lignin Procedures, *J. Sci. Food Agric.* 1994, 65, 51-58.
Hatfield et al., Degradation Characteristics of Isolated and In Situ Cell Wall Lucerne Pectic Polysaccharides by Mixed Ruminal Microbes, *J. Sci. Food Agric.* 1995, 69, 185-196.
Hatfield et al., Composition of cell walls isolated from cell types of grain sorghum stems, *J. Sci. Food Agric.* 1999, 79, 891-899.
Hatfield et al., Using the Acetyl Bromide Assay to Determine Lignin Concentrations in Herbaceous Plants: Some Cautionary Notes, *J. Agric. Food Chem.* 1999, 47, 628-632.
Hsiao et al., Lignans From the Wood of *Aralia Bipinnata*, *Phytochemistry* 1995, 39, 899-902.
Kim et al., Solution-state 2D NMR of Ball-milled Plant Cell Wall Gels in DMSO-$d_6$, *Bioenerg. Res.* 2008, 1, 56-66.
Kubes et al., Alkaline Pulping with Additives. A Review., *Wood Sci. Technol.* 1980, 14, 207-228.
Li et al., Time-Course Accumulation of Main Bioactive Components in the Rhizome of *Ligusticum chuanxiong*, *Planta Med.* 2005, 72, 278-280.
Lu et al., Facile Synthesis of 4-Hydroxycinnamyl p-Coumarates, *J. Agric. Food Chem.* 1998, 46, 2911-2913.
Lu et al., Highly Selective Syntheses of Coniferyl and Sinapyl Alcohols, *J. Agric. Food Chem.* 1998, 46, 1794-1796.
Lu et al., 13th International Symposium on Wood, Fiber, and Pulping Chemistry, Auckland, New Zealand, May 16-19, 2005, APPITA: Auckland, New Zealand, 2005; pp. 233-237.
Majcherczyk et al., Size-exclusion Chromatography of Lignin as ion-pair complex, *J. Chromatogr., A* 1997, 764, 183-191.
Murnen et al., Optimization of Ammonia Fiber Expansion (AFEX) Pretreatment and Enzymatic Hydrolysis of *Miscanthus × giganteus* to Fermentable Sugars, *Biotechnol. Prog.* 2007, 23, 846-850.
Oosterveld et al., Formation of ferulic acid dehydrodimers through oxidative cross-linking of sugar beet pectin, *J. Carbohydr. Res.* 1997, 300, 179-181.
Paula et al., Lignans from *Ochroma lagopus* Swarta, *Tetrahedron* 1995, 51, 12453-12462.
Ralph et al., Lignin-Feruloyl Ester Cross-links in Grasses. Part 1. Incorporation of Feruloyl Esters into Coniferyl Alcohol Dehydrogenation Polymers, *J. Chem. Soc., Perkin Trans. 1* 1992, 2961-2969.
Ralph et al., Pathway of p-Coumaric Acid Incorporation into Maize Lignin as Revealed by NMR, *J. Am. Chem. Soc.* 1994, 116, 9448-9456.
Ralph et al., Lignin-Ferulate cross-links in grasses: active incorporation of ferulate polysaccharide esters into ryegrass lignins, *Carbohydrate Research* 1995, 275, 167-178.
Ralph et al., Lignins: Natural polymers from oxidative coupling of 4-hydroxyphenyl-propanoids, *Phytochemistry Rev.* 2004, 3, 29-60.
Ralph et al., http://ars.usda.gov/Services/ docs.htm?docid)10429, 2005.
*SAS*, PC Windows Version 9.1.3; SAS Institute Inc.: Cary, NC, 2003.
Seca et al., Phenolic constituents from the core of Kenaf (*Hibiscus cannabinus*). *Phytochemistry* 2001, 56, 759-767.
Selvendran et al., Developments in the Isolation and Analysis of Cell Walls From Edible Plants, in *Biochemistry of Plant Cell Walls*; Brett, C. T., Hillman, J. R., Eds.; Cambridge University Press: Cambridge, 1985; pp. 39-78.
Shatalov et al., *Arundo donax* L. reed: new perspectives for pulping and bleaching. Part 4. Peroxide bleaching of organosolv pulps., *Bioresour. Biotechnol.* 2005, 96, 865-872.
Shea et al., Characterization of a Pectic Fraction from Smooth Bromegrass Cell Walls Using an Endopolygalacturonase, *J. Agric. Food Chem.* 1993, 41, 380-387.

* cited by examiner

Table 1. Concentrations (mg/g) of Lignin,[1] Alkali-Labile Ferulates,[2] and Total Ferulates[3] in Cell Walls[4]

| coniferyl ferulate (%) | lignin | | | alkali-labile ferulates | | | | total ferulates |
|---|---|---|---|---|---|---|---|---|
| | mass | klason | AcBr | monomers | dimers | coupled | total | |
| 0 | 186.3 | 199.4$^a$ | 203.0$^a$ | 0.37$^d$ | 0.66$^d$ | 0.14$^d$ | 1.17$^d$ | 13.1$^d$ |
| 20 | 165.9 | 173.5$^{ab}$ | 183.1$^b$ | 1.72$^c$ | 1.22$^c$ | 1.06$^c$ | 4.00$^c$ | 33.0$^c$ |
| 40 | 164.8 | 168.9$^b$ | 165.2$^{bc}$ | 4.35$^b$ | 2.57$^b$ | 1.98$^b$ | 8.92$^b$ | 52.1$^b$ |
| 60 | 163.9 | 157.1$^b$ | 160.6$^c$ | 6.57$^a$ | 3.62$^a$ | 2.77$^a$ | 12.96$^a$ | 72.2$^a$ |

[1] Lignin content was estimated from the mass of monolignols polymerized into cell walls and by Klason and acetyl bromide (AcBr) analysis of cell walls. [2] Alkali-labile ferulate released in the form of ferulate monomers, ferulate dimers, and ferulate cross-coupled to coniferyl alcohol. [3] Total quantity of ferulates in lignified cell walls (esterified to cell wall xylans and incorporated into lignin as coniferyl ferulate). [4] From maize cell suspensions artificially lignified with coniferyl alcohol and 0–60% coniferyl ferulate. [5] Means within columns with unlike superscripts differ ($P < 0.05$).

FIG. 4

Table 2. Concentrations (mg/g) of Alkali Soluble Lignin, Alkali-Soluble Carbohydrate, and Alkali-Insoluble Residue[1]

| coniferyl ferulate (%) | alkali-soluble lignin | | | alkali-soluble carbohydrate | | | alkali-insoluble residue | | |
|---|---|---|---|---|---|---|---|---|---|
| | 30 °C | 100 °C | 160 °C | 30 °C | 100 °C | 160 °C | 30 °C | 100 °C | 160 °C |
| 0 | 66[a,b] | 117[b] | 141[a] | 78[d] | 226[d] | 361[e] | 856[a] | 657[a] | 497[a] |
| 20 | 57[b] | 113[b] | 140[a] | 142[c] | 355[c] | 456[d] | 801[b] | 532[b] | 404[b] |
| 40 | 68[b] | 127[b] | 149[a] | 184[b] | 440[b] | 528[c] | 749[c] | 433[c] | 324[bc] |
| 60 | 106[a] | 149[a] | 159[a] | 178[b] | 476[a] | 583[b] | 716[d] | 375[d] | 259[c] |
| NL | ND | ND | ND | 354[a] | 632[a] | 698[a] | 646[e] | 368[d] | 302[c] |

[1] Derived from maize cell walls treated with 0.5 M aqueous NaOH at 30, 100, or 160 °C. Nonlignified (NL) cell walls isolated from maize cell suspensions were artificially lignified with coniferyl alcohol and 0 to 60% coniferyl ferulate. ND, not determined. [2] Means within columns with unlike superscripts differ (P < 0.05).

FIG. 6

Table 3. Carbohydrate (mg/g) Released from Maize Cell Walls (CW) and Alkali-Insoluble Residues (AIR) by Enzymatic Hydrolysis, and Carbohydrate (mg/g) Released Enzymatically from AIR Plus Alkali-Soluble Carbohydrate (AIR+ASC)[1]

| coniferyl ferulate (%) | 2 h enzymatic hydrolysis | | | | 48 h enzymatic hydrolysis | | | |
|---|---|---|---|---|---|---|---|---|
| | CW | AIR | AIR[2] | AIR+ASC[2] | CW | AIR | AIR[2] | AIR+ASC[2] |
| 0 | 244[3,c] | 460[c] | 393[c] | 471[c] | 521[c] | 671[d] | 574[a] | 652[d] |
| 20 | 294[bc] | 573[bc] | 459[b] | 602[b] | 551[bc] | 703[cd] | 563[a] | 706[c] |
| 40 | 325[b] | 665[ab] | 497[a] | 675[b] | 578[b] | 777[bc] | 582[a] | 766[b] |
| 60 | 351[b] | 692[ab] | 497[a] | 681[b] | 587[b] | 799[b] | 571[a] | 749[bc] |
| NL | 664[a] | 838[a] | 541[a] | 895[a] | 777[a] | 914[a] | 590[a] | 944[a] |

[1] Nonlignified (NL) cell walls isolated from maize cell suspensions were artificially lignified with coniferyl alcohol and 0–60% coniferyl ferulate. Cell walls and AIR prepared with aqueous 0.5 M NaOH at 30 °C were treated with commercial enzymes containing cellulase, hemicellulase, and pectinase activities. [2] Carbohydrate released on a whole cell wall basis. [3] Means within columns with unlike superscripts differ ($P < 0.05$).

FIG. 10

METHOD FOR MODIFYING LIGNIN STRUCTURE USING MONOLIGNOL FERULATE CONJUGATES

CROSS-REFERENCE TO RELATED APPLICATIONS

This application claims priority under 35 USC §119(e) to U.S. Provisional Patent Application 61/213,706 filed Jul. 6, 2009, the entirety of which is incorporated herein by reference.

REFERENCES

All of the documents cited herein are incorporated herein by reference.

INTRODUCTION

Lignin is a highly complex, heterogeneous polymer found in all vascular plants. It rigidifies plants and plays a crucial role in water transport. Lignin is notable for its complex structure. It is comprised predominately from three monomers, p-coumaryl alcohol 1, coniferyl alcohol 2, and sinapyl alcohol 3, and a host of other structurally related monomers. See FIG. 1. Other typical monomers found in natural lignins include 5-hydroxyconiferyl alcohol, hydroxycinnamaldehydes, hydroxybenzaldehydes, arylglycerols, tyramine hydroxycinnamates, hydroxycinnamic acids, hydroxycinnamate esters, dihydro-hydroxycinnamyl alcohols, arylpropane-1,3-diols, and various acylated monolignols-hydroxycinnamyl acetates, hydroxycinnamyl-p-hydroxybenzoates, and hydroxycinnamyl-p-coumarates. Hydroxycinnamaldehydes and their corresponding hydroxybenzaldehydes are found in all lignins. Hydroxycinnamyl acetates are found in most hardwoods and are present in high levels in kenaf and palms. Hydroxycinnamyl p-hydroxybenzoates are found in willows, palms, poplars, and aspens. Hydroxycinnamyl p-coumarates are found in all grasses. These monomers are polymerized into polymeric lignin by combinatorial radical coupling reactions. The lignification of cell walls is also notable because it is likely the single most important factor that limits forage digestibility in ruminants and the "saccharification" of plant polysaccharides to simple sugars for use in biofuel or biochemical applications. Practically speaking, lignin is indigestible in the digestive tract of ruminants. The interfering presence of indigestible lignin limits the ability of ruminants to utilize otherwise digestible carbohydrates present in the forage they eat. Lignin also limits enzyme access to cell wall polysaccharides, inhibiting the release of monosaccharides for conversion to other products including biofuels. Thus, there remains a long-felt and unmet need to alter lignins in such a way that improves the digestibility/fermentability of the cell wall polysaccharides.

Over the past decade it has become apparent that the metabolic malleability of lignification, the process of polymerization of phenolic monomers to produce lignin polymers, provides enormous potential for engineering the troublesome polymer to be more amenable to processing. Massive compositional changes can be realized by perturbing single genes in the monolignol pathway, particularly the hydroxylases (Ralph, et al. *Phytochem. Revs.* (2004), 3(1), 29-60; Boerjan, et al. *Annu. Rev. Plant Biol.* (2003), 54, 519-549; Marita, et al. *Proc. Natl. Acad. Sci.* (1999), 96(22), 12328-12332; Franke, et al. *Plant J.* (2002), 30(1), 47-59). The chemical nature of lignification, involving combinatorial radical coupling of monomers (primarily with the growing polymer) without direct enzymatic control, allows compatible phenolic compounds present in the cell wall (CW) during lignification to be incorporated into the "lignin" polymer. Novel (non-monolignol) monomers available to the plant, discovered in lignins from studies on the down-regulation of genes in the monolignol pathway, include products of incomplete monolignol biosynthesis such as 5-hydroxyconiferyl alcohol (COMT-deficiency), and coniferaldehyde and sinapaldehyde (CAD-deficiency) (Ralph et al. *Phytochem.* (2001), 57(6), 993-1003). These compounds couple integrally (via a radical route) into the lignin polymer. The list of other compounds found integrated into lignins in normal and/or transgenic plants is growing (Boerjan, et al. *Annu. Rev. Plant Biol.* (2003), 54, 519-549).

Observations to date have allowed the present inventors to detail the ideal properties of monolignol substitutes (Ralph, J., What makes a good monolignol substitute? In *The Science and Lore of the Plant Cell Wall Biosynthesis, Structure and Function*, Hayashi, T., Ed. Universal Publishers, Brown-Walker Press: Boca Raton, Fla., (2006); pp 285-293). When such compounds are introduced into lignins, even at significant levels, the plants often show no obvious growth/development phenotype. Monomers that have accessible conjugation into the sidechain allowing for so-called "endwise" β-O-4-coupling seem to fare the best. Examples are: 5-hydroxyconiferyl alcohol, the hydroxycinnamaldehydes, hydroxycinnamate esters, and acylated hydroxycinnamyl alcohols. Due to incompatibilities in radical coupling reactions, p-hydroxyphenyl moieties fare less well than guaiacyl or syringyl moieties, at least when incorporating into guaiacyl-syringyl lignins, but other phenolics have not been well studied.

Replacing the entire monomer component of lignification with a novel monomer is unlikely to be an effective strategy that is "acceptable" to the growing plant. Introducing strategic monomers into the normal monolignol pool is, however, a viable proposition as shown by the Examples described herein. Incorporation of novel monomer residues into lignin as described herein has produced plants with no pleiotropic effects or obvious growth phenotypes. Incorporation of up to 60% novel monomer residues into lignin has been accomplished. A range of alternative monomers are shown herein to be consistent with maintaining the plant's structural and functional integrity. Thus, the crux of the present invention is a method of manufacturing modified lignin using monomer-conjugate substitution (as well as the resulting modified lignin polymer itself). The resulting modified lignin drastically eases processing of the cell wall to yield value-added products, such as animal feeds and forages, pulps for papermaking, fermentable substrates for biofuel and chemical production, and the like.

SUMMARY OF THE INVENTION

Disclosed and claimed herein is a method of manufacturing modified lignin, the lignin so produced, and isolated cell walls incorporating the modified lignin.

Specifically, a first version of the invention is directed to an isolated lignified plant cell wall comprising lignin, wherein the lignin includes a ferulate residue incorporated therein. In a preferred version, the ferulate residue is introduced via monolignol-ferulate conjugates selected from the group consisting of coniferyl ferulate, sinapyl ferulate, and other structurally related conjugates.

The plant cell wall from which the lignin is isolated may be derived from any plant source, without limitation. That is, the plant cells themselves may be derived from any species of the Plantae kingdom that is now known to make lignin naturally, is discovered in the future to make lignin naturally, or does not make lignin naturally, but has been genetically modified to make lignin, without limitation. The plant cells may also be derived from plants that have been genetically modified for other purposes. This includes vascular plants of all description, monocots and dicots, hardwood and softwood trees, shrubs, grasses, grains, fruits, vegetables, etc. Preferred sources are grasses such as maize, *Miscanthus*, sorghum, and switchgrass, and trees, such as trees of the family Myrtaceae, or hybrids thereof, including trees of the genera *Eucalyptus, Corymbia*, and *Angophora*, as well as trees of the family Salicaceae, including trees of the genera *Populus* (e.g., poplar, aspen, and cottonwood trees, etc.), and *Salix* (e.g., willow trees), or hybrids of any of the foregoing.

The preferred ferulate monomer conjugates are coniferyl ferulate and sinapyl ferulate.

Another version of the invention is directed to a method of manufacturing modified lignin. Here, the method comprises conducting a lignin-producing polymerization reaction in the presence of at least one polymerizable conjugate (preferably coniferyl ferulate and/or sinapyl ferulate) comprising a hydroxycinnamic or hydroxybenzoic acid (or a hydroxyl, alkyl, alkyloxy, alkanoyl, or alkanoyloxy derivative thereof) esterified to a hydroxycinnamyl or benzyl alcohol (or a hydroxyl, alkyl, alkyloxy, alkanoyl, alkanoyloxy, derivative thereof) wherein at least one of the polymerizable conjugates is incorporated into the resulting lignin. Again, the preferred conjugates are coniferyl ferulate and sinapyl ferulate. It is preferred that from about 10% by wt to about 60% by wt of the polymerizable conjugates are reacted in the polymerization reaction. The polymerization reaction is conducted in vitro or in vivo.

In one specific version of the invention, the polymerization reaction comprises isolating a cell wall from a plant cell suspension and lignifying the cell wall in the presence of the polymerizable conjugate.

Included within the scope of the invention disclosed and claimed herein is the modified lignin produced by the process.

As noted above, it is generally preferred that from about 10% by wt to about 60% by wt of the polymerizable conjugates are reacted in the polymerization reaction, although ranges above and below the stated range are explicitly within the scope of the method (e.g., from 0.1 wt % to 100 wt %).

Also disclosed herein are isolated lignified cell walls containing a compound as recited above, wherein the compound is incorporated into the lignin of the cell wall. Likewise disclosed herein are isolated plant cells containing a compound as recited above, wherein the compound is incorporated into lignin in cell walls of the isolated plant cells.

The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above containing one or more double bonds. Examples of alkenyl groups include vinyl, 2-propenyl, crotyl, 2-isopentenyl, 2-(butadienyl), 2,4-pentadienyl, 3-(1,4-pentadienyl), etc., and higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another substituent means a divalent radical derived from an alkyl, alkenyl, or alkynyl group, respectively, as exemplified by —$CH_2CH_2CH_2CH_2$—.

The term "hydroxy" is used herein to refer to the group —OH.

The term "alkoxy" is used herein to refer to the —OR group, where R is alkyl, alkenyl, or alkynyl, or a substituted analog thereof. Suitable alkoxy radicals include, for example, methoxy, ethoxy, t-butoxy, etc. The term "alkoxyalkyl" refers to ether substituents, monovalent or divalent, e.g. —$CH_2$—O—$CH_3$ and —$CH_2$—O—$CH_2$—.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

BRIEF DESCRIPTION OF THE DRAWINGS

FIG. 4: Table 1. Concentrations (mg/g) of lignin, alkali-labile ferulates, and total ferulates in cell walls.

FIG. 6: Table 2. Concentrations (mg/g) of alkali-soluble lignin, alkali-soluble carbohydrate, and alkali-insoluble residue.

FIG. 10: Table 3. Carbohydrate (mg/g) released from maize cell walls and alkali-insoluble residues (AIR) by enzymatic hydrolysis, and carbohydrate (mg/g) released enzymatically from AIR plus alkali-soluble carbohydrate (AIR+ASC).

DETAILED DESCRIPTION

Figure 1:
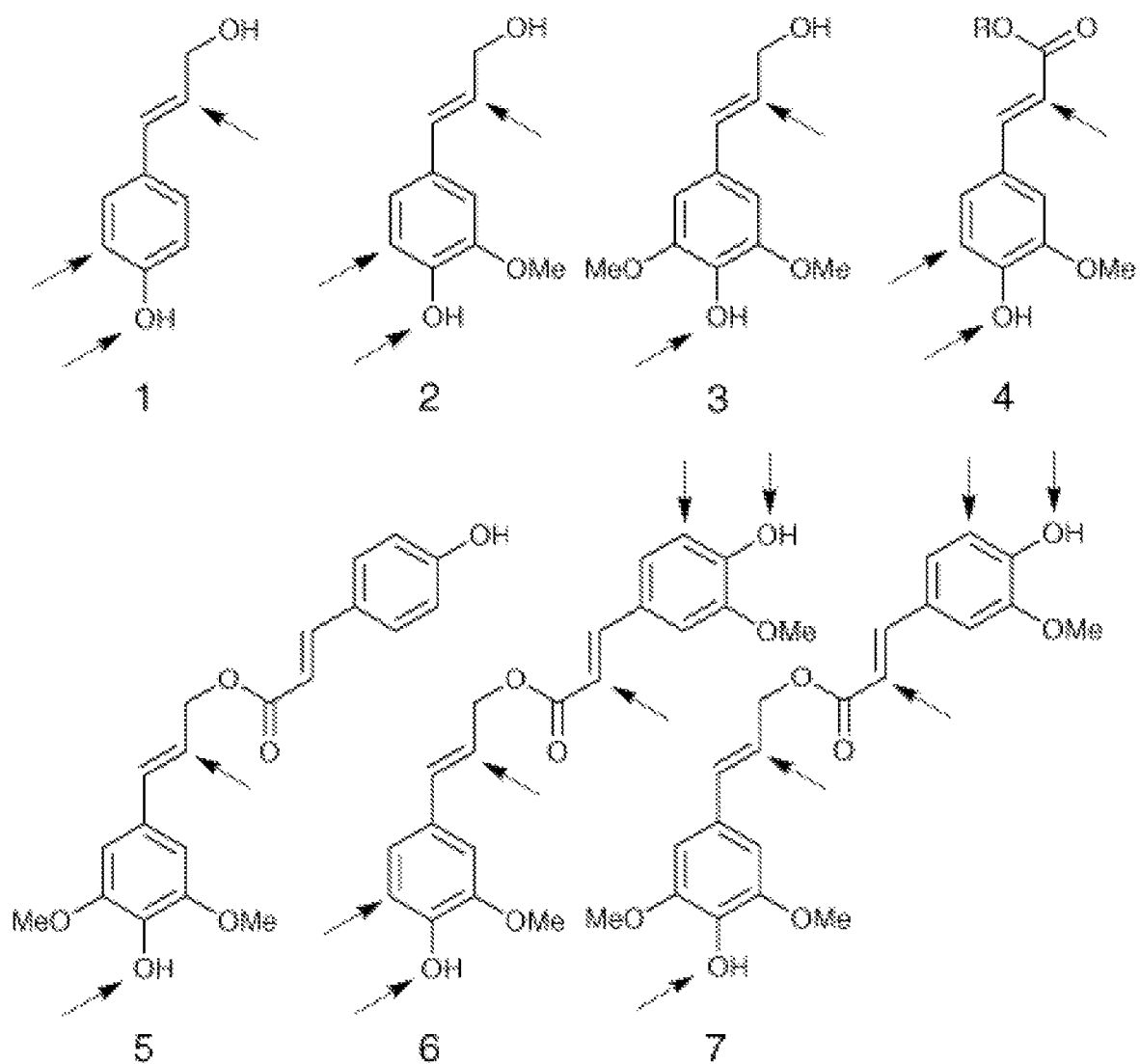
FIG. 1: Structures of p-coumaryl alcohol 1, coniferyl alcohol 2, sinapyl alcohol 3, ferulate 4, sinapyl p-coumarate 5, coniferyl ferulate 6, and sinapyl ferulate 7. Arrows indicate sites normally involved in radical coupling reactions during lignification.

Novel monomers that appear to be well suited for lignification can be found throughout the plant kingdom. Several groups of compounds, as described below, are suitable for producing modified lignins. As a general proposition, the most suitable monomer for producing modified lignins fall into five (5) classes: (1) bifunctional monomers or monomer conjugates linked via cleavable ester or amide bonds; (2) monomers that produce novel cleavable functionalities in the lignin polymer; (3) hydrophilic monomers; (4) monomers that minimize lignin-polysaccharide cross-linking; and (5) monomers that produce simpler lignins. Each of these classes of monomers will be described below. In each instance, suitable monomers are polymerized into a modified lignin. The modified lignins are then assessed to see whether and how the modified lignins impact biomass processing in biomimetic cell wall systems.

Many of the experimental procedures referenced herein are described only briefly. Full-text references describing the known procedures can be found at: http://www.dfrc.ars.usda.gov/DFRCWebPDFs/pdfindex.html.

Classes of Monomers to Consider:

Without regard to plant biochemistry, it is straightforward to propose suitable monomers from simple chemical principles. However, the only monomers that should be considered are those that plants can biosynthesize; i.e., those compounds for which biosynthetic pathways exist. The following five classes of monomers are preferred for use in the present invention:

Bifunctional Monomers or Monomer Conjugates Linked Via Cleavable Ester or Amide (and/or Hydrophilic) Functionality:

Monomers or conjugates with compatible phenolic groups at both ends are introduced into the lignin polymer. Using these types of bifunctional monomers allows lignification to proceed in both directions to incorporate the monomer. If coupling at the sidechain β-position is possible, such units can form important branch-points in the polymer. More importantly, if these units are linked by linkages that are readily cleaved during anticipated processing, they introduce groups into the polymer allowing it to be readily "unzipped"—i.e., depolymerized. As a result, delignification can therefore be achieved under less stringent conditions, releasing the polysaccharides with lower energy requirements and higher yields.

Diferuloylated Compounds:

Ferulates incorporate integrally into lignins by the same types of radical coupling reactions that typify lignification (Ralph, J. et al. *Phytochem. Revs.* (2004), 3(1), 79-96). Due to the combinatorial nature of such coupling reactions, the array of products is quite complex, but readily determined by NMR experiments. Having two ferulates in a monolignol-substitute allows lignification to proceed from both. The advantage is that, even after both ferulates have been integrally incorporated into the complex polymer, simply cleaving the esters then cleaves the polymer into fragments of lower molecular weight allowing their removal from the polysaccharides in the wall.

Bi-phenolic Conjugates:

Compounds that have two lignin-compatible moieties directly connected via cleavable functionality can also be incorporated into a modified lignin. For example, 3-methoxy-tyramine ferulate, unlike its tyramine ferulate analog, will polymerize integrally into lignins at both ends. The benzylic-$CH_2$ means that the monomer unit may undergo some further conversion, via a quinone methide, to the benzylic-OH analog first, but both this product and the parent will lignify. This benzylic conversion is analogous to the incorporation of dihydroconiferyl alcohol, and the derived guaiacylpropane-1,3-diol, into pine lignins, particularly in a CAD-deficient pine that produces enhanced levels of dihydroconiferyl alcohol monomer (Ralph, J. et al. *Org. Lett.* (1999), 1(2), 323-326; Ralph, J. et al. *Science* (1997), 277, 235-239). However, unlike dihydroconiferyl alcohol monomer, which can only appear as an end-unit in lignins, the difunctional nature of methoxytyramine ferulate means that it can become fully integrated into the polymer chain. The monomer has built-in bi-functionality. Finally, there are various ways of cleaving amides under mild conditions. Utilization of this monomer-substitute therefore is a way of introducing bond into the resultant lignin that can be readily cleaved during processing.

In this class are also various catechol derivatives, such as clovamide, caffeoyl 3-hydroxytyrosine, and rosmarinic acid. Catechol structures have not previously, however, been validated in lignins. Despite repeated attempts to find evidence for related caffeyl alcohol incorporation, even in CCOMT-deficient plants, there is currently no evidence for the natural incorporation of such non-methoxylated catechols into lignins. However, the related 3-methoxy-4,5-dihydroxy compounds (such as those produced in COMT-deficient plants that utilize 5-hydroxyconiferyl alcohol as a monomer) integrate readily. Thus, these compounds are suitable monomers for lignification. These monomers may prove more successful in p-hydroxyphenyl-rich lignification, in which case the target plants will also need to be C3H-deficient.

Methods for Testing Novel Lignification and the Resulting Biomass Processing Improvements:

Delineate Monomer Compatibility:

Determining the compatibility of the chosen monomers with lignification via in vitro model coupling reactions is essential to determine as any selected monomer that does not couple integrally into lignins is unlikely to be valuable. Coupling and cross-coupling propensities are best tested empirically as there do not appear to be any systematic rules the predict whether a monomer will couple and cross-couple appropriately. Such methods have been used to define how ferulates couple into lignins, for example (Ralph, J. et al. *J. Chem. Soc., Perkin Trans.* 1 (1992), (21), 2961-2969). The models and model polymers will also provide the NMR database required to identify how monomers incorporate into the more complex cell wall models and in transformed plants.

Biomimetically Lignify the Selected Monomers into Cell Walls:

Selected monomers, at varying levels relative to the normal monolignols, are incorporated into cell walls. Strategically $^{13}C$-labeled monomers are used as appropriate.

Delineate the Resultant Cell Wall Lignin Structure:

Structural characterization of the cell walls reveal whether the monomers integrate into wall lignins and also provide materials for conversion testing. Structures are examined by degradative methods and, most importantly, via the whole-cell-wall dissolution and NMR procedures (where the strategic labeling helps reveal the bonding patterns) (Lu, et al. *Plant J.* (2003), 35(4), 535-544).

Test Biomass Processing Impacts:

Monomers are selected for their potential to improve biomass processing efficiency. The cell walls created are tested under a variety of biomass conversion methods to delineate how much improvement might be expected in planta from utilization of the monomer substitutes are various levels.

These steps are described more fully below.

Delineating Monomer Compatibility:

Synthetic in vitro coupling reactions, although they do not provide materials suitable for testing the effects of lignin modification, play a valuable role in the initial selection of potential monomers. The reasoning is simple. All the coupling reactions evidenced in lignins in vivo are also produced, admittedly at different relative levels, in vitro. If coupling and cross-coupling compatibility is not observed in synthetic coupling reactions, failure in planta is almost certainly assured because the in vivo reaction is also purely chemical. Because the monomer-substitutes are envisioned to incorporate into lignification with the normal monolignols, it is important that they be compatible with coupling and, more importantly, cross-coupling reactions with the growing polymer derived in part from those monolignols.

It is for these reasons that some suggestions, seemingly logical on paper, will not function. For example, it has already been established that non-methoxylated phenolic entities such a tyramine and p-coumarate do not become integrated into the polymer by coupling reactions. They are found in lignin polymers, but only as "appendages" or end-units. For example, p-coumarates are exclusively found as acylating groups in lignin sidechain γ-positions. They are free-phenolic (non-etherified), meaning that they do not undergo radical coupling reactions. On their own, in vitro, p-coumarates will couple, but what happens during lignification in the presence of normal monolignols and lignin guaiacyl/syringyl units is that radical transfer from these less-stable radicals occurs before they will enter into radical coupling (Ralph, J. et al. *Phytochem. Revs.* (2004), 3(1), 79-96). Thus, lignifying with coniferyl- or sinapyl p-coumarate is known not to work. The coniferyl and sinapyl alcohol moieties incorporate as usual, but the p-coumarate end, despite being phenolic and potentially capable of radical coupling, will not incorporate—the units remain as free-phenolic pendant units. As a result, cleaving the esters will release the p-coumarate but will not cause any depolymerization of the polymer. Similarly, the idea of using tyramine ferulate will not work either; tyramine units (also non-methoxylated phenolics) do not enter into coupling reactions under normal in planta conditions (Ralph, J. et al. *Proc. Natl. Acad. Sci.* (1998), 95(22), 12803-12808). However, if lignins are derived from higher levels of the non-methoxylated monolignol, p-coumaryl alcohol, p-coumarates and tyramines will cross-couple into those p-hydroxyphenyl-rich polymers. Thus exploring the chemical compatibility of monomers first will delineate whether it is worth introducing those monomers into C3H-deficient plants, for example—plants in which the coniferyl and sinapyl alcohol levels are depleted at the expense of the potentially compatible p-coumaryl alcohol.

Although tyramine ferulate was noted as not being a candidate for introducing cleavable bonds into lignins, an analog can be found in certain plants. 3-Methoxytyramine ferulate is a bifunctional molecule in which both moieties are entirely compatible with lignification. It therefore incorporates fully, from both ends, into lignin. The cleavable amide functionality then introduced into the backbone of the polymer is exactly the kind of zipper unit that will allow such a polymer to be more readily depolymerized.

Biomimetic Lignification into Suspension-Cultured Cell Walls:

Once the monomers have been obtained/synthesized, they are then tested for their lignifying ability. As a general rule, it is not preferred to make synthetic lignins by simple in vitro polymerization of these monomers (with or without the traditional monomers) because the in vitro materials give little insight into the behavior of the cell wall during biomass processing. It is much preferred to produce cell walls lignified with the novel monomers (either in the presence of, or the absence of the normally present monolignols). A suspension-cultured corn system for producing cell walls amenable to controlled lignification by exogenously supplying the lignin monomers has been described. See Grabber, J. H. et al. *J. Agr. Food Chem.* (1996), 44(6), 1453-1459. The cell walls already contain the polysaccharide complement, and contain their own peroxidases. Compatible phenolic monomers and a supply of $H_2O_2$ are the only requirements to effect in muro lignification. When normal monolignols are fed, the lignins are structurally extremely similar to those in the analogous growing plant. A representative protocol is as follows: Primary cell walls (~1.2 g dry weight) isolated from 14 d old maize cell suspensions were stirred in 120 mL of HOMOPIPES buffer (25 mM, pH 5.5 with 4 mM $CaCl_2$) and artificially lignified over ~24 h by adding separate solutions of lignin precursors (250 mg in 70 mL of 35% (v/v) dioxane:water) and $H_2O_2$ (30%, 225 µL in 90 mL water, 1.1 eq) at 3 mL/h. In two separate runs of the experiment, guaiacyl-type lignin precursors consisting of 0, 20, 40, 60% and perhaps 100% (depending on the monomer), by weight, of monomer-substitute of interest mixed with coniferyl alcohol. Copolymerization of novel monomers with a mixture of coniferyl and sinapyl alcohols to form mixed syringyl-guaiacyl-based lignins may also be conducted (to better mimic lignification in dicots). Nonlignified controls are stirred in a solvent mixture similar to the final makeup of the lignification reaction media. Cell wall peroxidase activity during lignification is monitored with guaiacol-$H_2O_2$ staining. Although ideal for grasses, this system likely underestimates the improvements that can be realized in other angiosperms or in gymnosperms; for example, in chemical pulping, grass cell walls are already significantly more alkali-soluble than in other types of plants. It is therefore also planned to implement and use similar suspension-cultured systems such as the secondary wall producing systems from tobacco, poplar, as well as Wagner's pine tracheary element system. Such systems provide assorted lignified plant cell walls. See, respectively, Blee, et al. *Planta* (2001), 212(3), 404-415; Ohlsson, et al. *Protoplasma* (2006), 228(4), 221-229; and Wagner, et al. *Proc. Natl. Acad. Sci.* (2007), 104(28), 11856-11861.

Delineating Resultant Lignin Structure:

An important aspect of this work is in establishing how well the novel monomer incorporated into lignin. With model data from the model coupling reactions, NMR methods in particular, and degradative methods such as analytical thioacidolysis and the DFRC method, enable delineating how well incorporated a novel monomer becomes, and into what types of structures it is incorporated. See, respectively, Lapierre, et al., Application of new methods for the investigation of lignin structure. In *Forage Cell Wall Structure and Digestibility*, Jung, H. G.; Buxton, D. R.; Hatfield, R. D.; Ralph, J., Eds. ASA-CSSA-SSSA: Madison, Wis., (1993), pp 133-166; and Lu, et al., *J. Agr. Food Chem.* (1997), 45(7), 2590-2592. This provides particularly important data for delineating whether plant alteration has been successful. In addition to carefully evaluated individual spectra, emerging cell wall 2D NMR "fingerprint" profiles and chemometrics methods can be used to relate the detailed structural information available in the profile to various conversion parameters. See Lu & Ralph, *Plant J.* (2003), 35(4), 535-544; Hedenström, et al. *Molecular Plant* (2009) 2(5), 933-942.

Testing Biomass Processing:

More straightforward but no less important is the processing and testing of the cell walls with modified lignins to assess the impact of the lignification changes on biomass conversion efficiency. These processes are all well established and won't be detailed herein. For example, the ethanolysis process for producing cellulose that is ideal for saccharification and fermentation. See Pan, X. J. et al. *Biotechnol. Bioeng.* (2005), 90(4), 473-481.

The walls from above will be subjected to various biomass processing conditions, and compared to controls. To develop a comprehensive database of conditions, at least the following processing pretreatments should be tested: ethanolysis (and other organosolv methods; Pan, X. J., supra), aminolysis, including the AFEX (ammonia fiber expansion) process (Holtzapple, et al. *Appl. Biochem. Biotechnol* (1992), 0273-2289), alkaline pulping, and acid hydrolysis. An example protocol for processing via alkaline pulping is as follows: The alkaline solubility of lignins is determined by incubating cell walls under $N_2$ atmosphere with 100 mL/g of 0.5 M aqueous NaOH for 22 h at 30° C. or for 2.5 h at 100 or 160° C. Anthraquinone (0.02 mg/mL) is added to catalyze the hydrolysis of lignin ether inter-unit linkages at 160° C. After cooling, alkaline residues are pelleted (5,000×g, 15 min), resuspended in water, neutralized with acetic acid, and then repeatedly pelleted (5,000×g, 15 min) and resuspended in water before freeze-drying and weighing. Original cell walls and alkaline residues are analyzed for lignin by the acetyl bromide method. Alkaline hydrolysates are extracted into ethyl acetate containing 50 mM QAM, dried, and dissolved in THF to determine the molecular weight distribution of by SEC-HPLC. Various GC-MS analyses may also be performed depending on the monomer used. Enzymatic saccharification and simultaneous saccharification and fermentation will be compared on the products from these pretreatments, as well as directly on steam exploded material. One of the most convenient and high-throughput measures of ruminal fermentability, a gas-accumulation in vitro method, has been shown to correlate well with the fermentability of cellulosic biomass to ethanol (via simultaneous saccharification and fermentation).

Utility:

As shown in the Examples below, the initial results are quite favorable. For example, the potential energy savings afforded by the remarkable processing improvements on cell walls is tremendous. Such gains portend enormous potential for sustainable local (and even small-scale) processing without massive facility costs. A conventional pulp mill digester facility currently costs ~$1 billion, for example. Decreasing the need to transport low-density plant materials across large distances, by processing toward higher-density materials locally, can also be a huge factor in decreasing the total energy requirements of processing, with consequent major impact on reducing greenhouse emissions, particularly if fossil fuels remain in (partial) use for transport. These lignin-modified materials appear to be exactly what this industry requires. The present method thus has the potential to deliver quantum improvements in biomass processing compared to the more incremental changes that are envisioned from simply perturbing the known lignin monomer pathways.

In summary, the present method structurally alters lignin by altering its monomer complement to allow the biomass polysaccharides to be more efficiently and sustainably utilized.

Coniferyl Ferulate and Sinapyl Ferulate Incorporation into Lignin:

Recent discoveries highlighting the metabolic malleability of plant lignification indicate that lignin can be engineered to dramatically diminish its adverse impact on fiber utilization for nutritional and industrial purposes. Perturbing single genes in the monolignol pathway can lead to dramatic shifts in the proportions of normal monolignols (1, 2, 3; FIG. 1) polymerized into lignin or elevated incorporation of pathway intermediates into the polymer. In normal plants, monolignols destined for lignin polymerization can also be extensively acylated with acetate, p-hydroxybenzoate, or p-coumarate (Ralph, J.; Lundquist, K.; Brunow, G.; Lu, F.; Kim, H.; Schatz, P. F.; Marita, J. M.; Hatfield, R. D.; Ralph, S. A.; Christensen, J. H.; Boerjan, W. *Phytochem. ReV.* 2004, 3, 29-60).

p-Coumarates acylate the γ-position of phenylpropanoid sidechains of mainly syringyl units in lignin (Ralph, J.; Hatfield, R. D.; Quideau, S.; Helm, R. F.; Grabber, J. H.; Jung, H.-J. G. *J. Am. Chem. Soc.* 1994, 116, 9448-9456; Grabber, J. H.; Quideau, S.; Ralph, J. *Phytochemistry* 1996, 43, 1189-1194). Structural and enzymatic studies suggest that syringyl units are enzymatically pre-acylated with p-coumarate prior to their incorporation into lignin, see Lu, F.; Ralph, J. 13th International Symposium on Wood, Fiber, and Pulping Chemistry, Auckland, New Zealand, May 16-19, 2005, APPITA: Auckland, New Zealand, 2005; pp 233-237, implicating sinapyl p-coumarate 5 as the logical precursor. Based on the analysis of isolated lignins and whole cell walls, sinapyl p-coumarate could comprise up to 40% of the lignin in some grass tissues (Ralph, J.; Hatfield, R. D.; Quideau, S.; Helm, R. F.; Grabber, J. H.; Jung, H.-J. G. *J. Am. Chem. Soc.* 1994, 116, 9448-9456; and Hatfield, R. D.; Wilson, J. R.; Mertens, D. R. *J. Sci. Food Agric.* 1999, 79, 891-899). p-Coumarate esters on lignin form few cross-linked structures mediated by radical coupling reactions and most remain as terminal units with an unsaturated side chain and a free phenolic group (Ralph, J.; Hatfield, R. D.; Quideau, S.; Helm, R. F.; Grabber, J. H.; Jung, H.-J. G. *J. Am. Chem. Soc.* 1994, 116, 9448-9456).

In contrast to p-coumarate, ferulates 4 esterified by simple alcohols, sugars, soluble pectins, or insoluble cell-wall xylans readily undergo diverse radical coupling reactions with each other and with lignin monomers and oligomers to form cross-linked networks (Oosterveld, A.; Grabber, J. H.; Beldman, G.; Ralph, J.; Voragen, A. G. *J. Carbohydr. Res.* 1997, 300, 179-181; Grabber, J. H.; Hatfield, R. D.; Ralph, J.; Zon, J.; Amrhein, N. *Phytochemistry* 1995, 40, 1077-1082; Grabber, J. H.; Ralph, J.; Hatfield, R. D. *J. Agric Food. Chem.* 2000, 48, 6106-6113; Grabber, J. H.; Ralph, J.; Hatfield, R. D. *J. Agric. Food Chem.* 2002, 50, 6008-6016; and Ralph, J.; Helm, R. F.; Quideau, S.; Hatfield, R. D. *J. Chem. Soc., Perkin Trans.* 1 1992, 2961-2969). Once polymerized into lignin, ferulate cannot be fully released by solvolytic methods (Grabber, J. H.; Ralph, J.; Hatfield, R. D. *J. Agric Food. Chem.* 2000, 48, 6106-6113). Cleavage of ferulate ester linkages, however, contributes to the unusually high extractability of grass lignin and the dramatically improved enzymatic degradability of grass cell walls following mild alkaline treatments (Fahey, G. C., Jr.; Bourquin, L. D.; Titgemeyer, E. C.; Atwell, D. G. In *Forage Cell Wall Structure and Digestibility*; Jung, H. G., Buxton, D. R., Hatfield, R. D., Ralph, J., Eds.; Am. Soc. Agronomy: Madison, Wis., 1993; pp 715-766).

Figure 2:
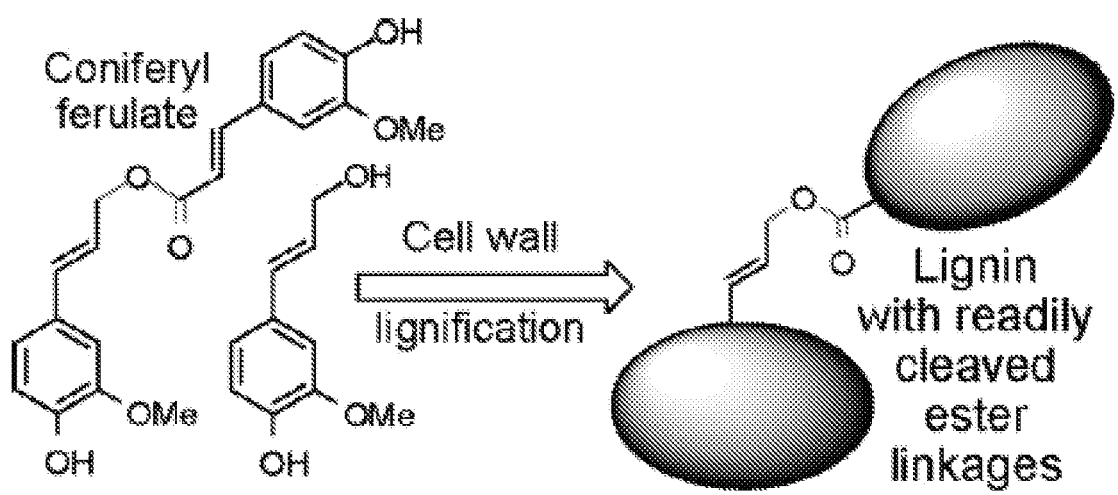
FIG. 2: Copolymerization of coniferyl ferulate with monolignols to form lignin with ester linkages in the backbone of the polymer. Such linkages facilitate lignin depolymerization during alkaline or acidic pretreatment of biomass for saccharification or paper production.

Ferulate-monolignol ester conjugates, such as coniferyl ferulate 6 or sinapyl ferulate 7 have not been identified in lignins, but they are naturally produced by some plants as secondary metabolites during, among other things, lignan biosynthesis (Paula, V. F.; Barbosa, L. C. A.; Howarth, O. W.; Demuner, A. J.; Cass, Q. B.; Vieira, I. J. C. *Tetrahedron* 1995, 51, 12453-12462; Seca, A. M. L.; Silva, A. M. S.; Silvestre, A. J. D.; Cavaleiro, J. A. S.; Domingues, F. M. J.; Pascoal-Neto, C. *Phytochemistry* 2001, 56, 759-767; Hsiao, J. J.; Chiang, H. C. *Phytochemistry* 1995, 39, 899-902; and Li, S. L.; Lin, G.; Tam, Y. K. *Planta Med.* 2005, 72, 278-280). This raises the exciting possibility that plants could be engineered to produce and transport coniferyl or sinapyl ferulate to the apoplastic space in a manner analogous to sinapyl p-coumarate, but with full incorporation of both the ferulate and the monolignol moieties of the conjugate into lignin (FIG. 2). Incorporating these conjugates or other related diphenolics will improve lignin extraction during alkaline pulping (Baucher, M.; Halpin, C.; Petit-Conil, M.; Boerjan, W. *Crit. ReV. Biochem. Mol. Biol.* 2003, 38, 305-350), via one or more of the following mechanisms: (1) cleavage of ester inter-unit linkages to depolymerize lignin; (2) improved lignin solubility due to ionization of ferulic acid groups; and (3) a smaller inherent size of lignins due to a steady supply of ferulates acting as new initiation sites for polymerization. Such lignins likely would also degrade more readily by acidic or alkaline processes used to pretreat lignocellulosic biomass for saccharification and fermentation to ethanol (Dien, B. S.; Jung, H. J. G.; Vogel, K. P.; Casler, M. D.; Lamb, J. F. S.; Iten, L.; Mitchell, R. B.; Sarath, G. *Biomass Bioenergy* 2006, 30, 880-891; and Murnen, H. K.; Balan, V.; Chundawat, S. P. S.; Bals, B.; Sousa, L. D.; Dale, B. E. *Biotechnol. Prog.* 2007, 23, 846-850). Because of these benefits, a well-developed biomimetic cell-wall model system (Grabber, J. H. *Crop Sci.* 2005, 45, 820-831) was used to test whether bioengineering of plants to incorporate coniferyl ferulate into lignin would enhance the delignification and enzymatic hydrolysis of cell walls.

EXAMPLES

The following Examples are included solely to provide a more complete disclose of the invention disclosed and claimed herein. The Examples do not limit the scope of the claimed invention in any fashion.

Cell Wall Lignification:

Freshly isolated primary cell walls (~1.05 g dry weight) from maize cell suspensions (Grabber, J. H.; Ralph, J.; Hatfield, R. D.; Quideau, S.; Kuster, T.; Pell, A. N. *J. Agric. Food Chem.* 1996, 44, 1453-1459) were stirred in 120 mL of homopiperazine-N,N'-bis-2-ethanesulfonic acid (Homopipes) buffer (25 mM, pH 5.5 with 4 mM $CaCl_2$) and artificially lignified by adding separate solutions of lignin precursors (250 mg in 70 mL of 35% (v/v) dioxane/water) and $H_2O_2$ (30%, 225 µL in 90 mL water, ~1.4 equiv) at 3 mL/h. Precursor mixtures were comprised of coniferyl alcohol substituted with 0, 20, 40, or 60% (by weight) of coniferyl-ferulate. Precursor treatments were replicated by carrying out two independent runs of the experiment. Precursors were also prepared in dioxane-water to maintain coniferyl ferulate in stable solutions. Lignin precursors were synthesized as described previously (Lu, F.; Ralph, J. *J. Agric. Food Chem.* 1998, 46, 2911-2913; and Lu, F.; Ralph, J. *J. Agric. Food Chem.* 1998, 46, 1794-1796). Nonlignified controls were stirred in a solvent mixture similar to the final makeup of the lignification reaction media. Cell wall peroxidase activity during lignification was monitored with guaiacol-$H_2O_2$ staining (Grabber, J. H.; Lu, F. *Planta* 2007, 226, 741-751). After additions were completed, cell walls were stirred for an additional 72 h before collection on glass-fiber filters (1.2 µm retention) and washed with water followed by acetone to remove nonincorporated lignin precursors. After evaporating off acetone in a hood, cell walls were dried at 55° C. and weighed. Filtrates were evaporated in vacuo to remove acetone and extracted with ethyl acetate to isolate nonincorporated precursors (and their coupling products). Ethyl acetate extracts were dried with anhydrous magnesium sulfate, filtered, evaporated in vacuo, and weighed. Nonincorporated precursors were then dissolved in DMSO and analyzed by $^1H$ NMR. In separate experiments, dehydrogenation polymers for use as analytical standards were formed in high yield (>94%) by slowly adding separate solutions of the aforesaid series of lignin precursors and $H_2O_2$ to stirred flasks containing HOMOPIPES buffer and horseradish peroxidase.

Similarly, in parallel runs, primary cell walls (~1.2 g dry weight) isolated from 14 day-old maize cell suspensions were stirred in 120 ml of Homopipes buffer (25 mM, pH 5.5 with 4 mM $CaCl_2$) and artificially lignified over 24 hours by adding separate solutions of lignin precursors (250 mg in 70 ml of 35% (v/v) dioxane:water) and $H_2O_2$ (30%, 225 µl in 90 ml water) at 3 ml/hour. In two separate runs of the experiment, guaiacyl-type lignin precursors consisted of 0, 20, 40 or 60% (by weight) of coniferyl ferulate mixed with coniferyl alcohol. In a third run, lignin precursors consisted of 0, 20, 40 or 60% (by weight) of sinapyl ferulate mixed with sinapyl and coniferyl alcohols. The quantities of the monolignols were adjusted to maintain an overall syringyl to guaiacyl unit ratio of 1:3 in each treatment. Non-lignified controls were stirred in a solvent mixture similar to the final makeup of the lignification reaction media. Cell wall peroxidase activity during lignification was monitored with guaiacol-$H_2O_2$ staining.

The alkaline solubility of lignins was determined by incubating cell walls under $N_2$ atmosphere with 100 ml/g of 0.5M aqueous NaOH for 22 hours at 30° C. or for 2.5 hours at 100° or 160° C. Anthraquinone (0.02 mg/ml) was added to catalyze the hydrolysis of lignin ether inter-unit linkages at 160° C. After cooling, alkaline residues were pelleted (5,000×g, 15 min), resuspended in water, neutralized with acetic acid, and then repeatedly pelleted (5,000×g, 15 min) and resuspended in water before freeze-drying and weighing. Original cell walls and alkaline residues were analyzed for lignin by the acetyl bromide method. Alkaline hydrolysates were extracted into ethyl acetate containing 50 mM QAM, dried, and dissolved in tetrahydrofuran (THF) to determine the molecular weight distribution of extracted lignins by SEC-HPLC. After adding 2-hydroxycinnamic acid as an internal standard, alkaline hydrolysates from the 30° C. incubations were acidified with HCl, extracted with ethyl ether, and silylated for GLC-FID analysis of ferulates and diferulates.

Cell Wall and Statistical Analyses:

The alkaline solubility of lignins was determined by incubating cell walls at 30° C. for 24 h, 100° C. for 2.5 h, or 160° C. for 2.5 h in sealed Teflon vials under $N_2$ using 0.5 M aqueous NaOH added at 100 mL/g of cell walls. Anthraquinone (0.02 mg/mL) was added to catalyze the hydrolysis of lignin ether interunit linkages at 160° C. (Kubes, G. J.; B. I., F.; MacLeod, J. M.; Bolker, H. I. *Wood Sci. Technol.* 1980, 14, 207-228). After cooling, alkali-insoluble residues were pelleted (5000×g, 15 min), resuspended in water, neutralized with acetic acid, and then repeatedly pelleted (5000×g, 15 min) and resuspended in water before freeze-drying and weighing. Alkaline hydrolysates recovered from cell walls (and from dehydrogenation polymers subjected to the same series of alkaline treatments) were scanned from 250 to 400 nm with a spectrophotometer. Alkaline hydrolysates were also extracted into ethyl acetate containing 50 mM tricaprylylmethyl ammonium chloride, dried, and dissolved in THF to determine the molecular weight distribution of extracted lignins by size exclusion high-performance liquid chromatography (SECHPLC) (Majcherczyk, A.; Huttermann, A. *J. Chromatogr., A* 1997, 764, 183-191). After adding 2-hydroxycinnamic acid as an internal standard, alkaline hydrolysates from the 30° C. incubations were acidified with HCl, extracted with ethyl ether, and silylated for gas-liquid chromatography with flame-ionization detection (GLC-FID) analysis of ferulates and diferulates using previously determined response factors (Grabber, J. H.; Ralph, J.; Hatfield, R. D. *J. Agric Food. Chem.* 2000, 48, 6106-6113). Response factors of ferulate-coniferyl alcohol dimers were assumed to be similar to diferulates.

Cell walls and alkali-insoluble residues were analyzed for lignin by the acetyl bromide method (Hatfield, R. D.; Grabber, J. H.; Ralph, J.; Brei, K. *J. Agric. Food Chem.* 1999, 47, 628-632), using dehydrogenation polymers as standards. Cell walls were also analyzed for acid-insoluble lignin by the Klason method (Hatfield, R. D.; Jung, H. G.; Ralph, J.; Buxton, D. R.; Weimer, P. J. *J. Sci. Food Agric.* 1994, 65, 51-58). Whole cell walls (~40 mg) were sonicated in 1-2 mL of DMSO-d6 and subjected to gel-state NMR using a cryoprobe 750 MHz (DMX-750) Bruker Biospin (Rheinstetten, Germany) instrument as described by Kim et al, *Bioenerg. Res.* 2008, 1, 56-66.

Original cell walls and alkali-insoluble residues collected from 30° C. alkaline incubations were suspended (0.5% w/v) in 20 mM MES buffer (pH 5.5, 40° C.) and hydrolyzed with a mixture of "CELLUCLAST 1.5 L" enzyme, "VISCOZYME L" enzyme (each added at 80 μL/g cell wall), and "BIOFEED BETA" enzyme (added at 80 mg/g cell wall). These are commercial enzymes marketed by Novo Nordisk, Bagsvaerd Denmark. This mixture of enzymes was selected to provide a broad complement of cellulase, hemicellulase, and pectinase activities for degrading lignocellulosic material (Grabber, J. H.; Ralph, J.; Hatfield, R. D. *J. Agric. Food Chem.* 1998, 46, 2609-2614). After 2 and 48 h of enzymatic hydrolysis, residues were pelleted by centrifugation (2 min, 10000× g) and an aliquot of the supernatant was analyzed for uronosyls by a colorimetric method (Blumenkrantz, N.; Asboe-Hansen, G. *Anal. Biochem.* 1973, 54, 484-489; and Shea, E. M.; Hatfield, R. D. *J. Agric. Food Chem.* 1993, 41, 380-387) and for neutral sugars by a Dionex BioLC (Dionex Corporation, Sunnyvale, Calif.), (Hatfield, R. D.; Weimer, P. J. *J. Sci. Food Agric.* 1995, 69, 185-196).

Data were analyzed according to a randomized complete block design with two replications using PROC GLM (SAS, PC Windows Version 9.1.3; SAS Institute Inc.: Cary, N.C., 2003). Means were subjected to pair-wise comparisons by the LSD procedure when a significant F-test was detected at $P<0.05$. Unless noted otherwise in the text, all reported differences were significant at $P<0.05$.

Results and Discussion of Examples:

Cell Wall Lignification.

In the Examples, varying proportions of coniferyl alcohol and coniferyl ferulate were polymerized into nonlignified primary walls of maize via wall-bound peroxidase and exogenously supplied $H_2O_2$. Previous work has demonstrated that artificial lignins formed by this system are structurally similar to those naturally formed in grasses (Grabber, J. H.; Ralph, J.; Hatfield, R. D.; Quideau, S.; Kuster, T.; Pell, A. N. *J. Agric. Food Chem.* 1996, 44, 1453-1459). Based on mass-balance calculations, the incorporation of precursors into wall-bound lignin declined from 92 to 72% in the first and from 100 to 94% in the second run of the experiment as the proportion of coniferyl ferulate increased from 0 to 60%. While both runs were conducted in an identical manner, guaiacol staining (data not shown) revealed that poorer incorporation of precursors in the first run of the experiment was associated with lower cell wall peroxidase activity at the end of lignification. As noted in a previous study with a structurally related sinapyl p-coumarate ester (Grabber, J. H.; Lu, F. *Planta* 2007, 226, 741-751), depressed incorporation of precursors associated with coniferyl ferulate addition was related to an accelerated loss of cell wall peroxidase activity. Because nonbound apoplastic peroxidases were removed prior to artificial lignification (Grabber, J. H.; Ralph, J.; Hatfield, R. D.; Quideau, S.; Kuster, T.; Pell, A. N. *J. Agric. Food Chem.* 1996, 44, 1453-1459), peroxidase inactivation would be more markedly manifested in the model system than in plants.

Figure 3:
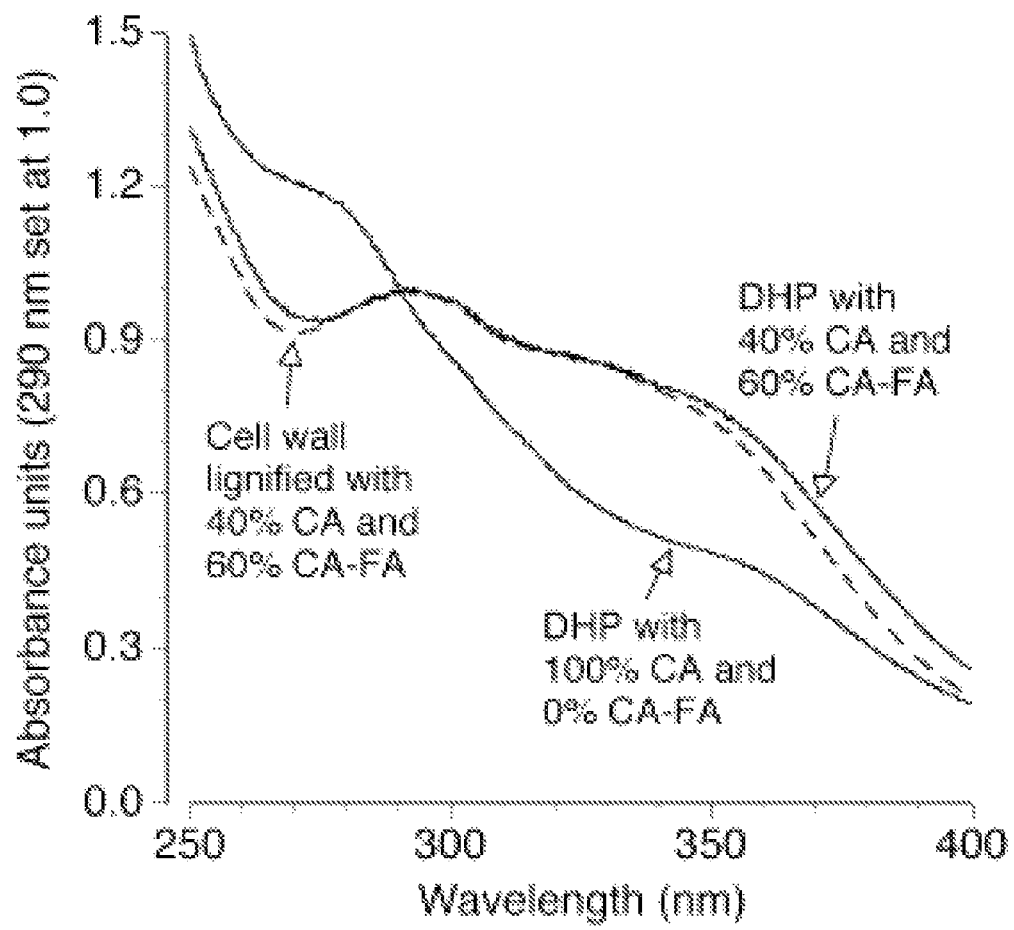
FIG. 3: UV spectra of cell wall and dehydrogenation polymer (DHP) lignins prepared with coniferyl alcohol (CA) and coniferyl ferulate (CA-FA) and fully solubilized by 0.5 M aqueous NaOH at 160° C.

Based on $^1$H NMR analysis (data not shown), nonbound precursors recovered after lignification were ~1.4-fold enriched in ferulate compared to the original precursor mixture, indicating that coniferyl ferulate was incorporated somewhat less efficiently than coniferyl alcohol into wall bound lignins. Extensive copolymerization of coniferyl ferulate into cell wall lignins was, however, readily apparent by gel-state 2D NMR of whole cell walls (data not shown) and from UV spectra of alkali-soluble lignins fully solubilized at 160° C. from cell walls (FIG. 3).

The average mass-balance lignin content of cell walls declined numerically from 186 to 164 mg/g as the proportion of coniferyl ferulate increased (see Table 1 shown in FIG. 4). Due to the incorporation of matrix components into lignin (Grabber, J. H.; Ralph, J.; Hatfield, R. D.; Quideau, S.; Kuster, T.; Pell, A. N. *J. Agric. Food Chem.* 1996, 44, 1453-1459), cell walls lignified with coniferyl alcohol had higher Klason and acetyl bromide lignin concentrations than that predicted by mass balance calculations. The Klason and acetyl bromide methods also indicated a greater decline in lignin content due to coniferyl ferulate addition. For the acid-insoluble Klason method, this decline is due to ester cleavage and loss of free ferulic acid from lignins formed with coniferyl ferulate. The spectrophotometric acetyl bromide method is sensitive to changes in lignin composition, including the presence of p-hydroxycinnamate esters on lignin (Fukushima, R. S.; Hatfield, R. D. *J. Agric. Food Chem.* 2004, 52, 3713-3720). To account for shifts in UV absorption coefficients in the acetyl bromide assay, dehydrogenation polymers prepared with 0-60% coniferyl ferulate were used as standards. While these polymers provide a good estimate, this may not fully account for spectral properties of lignin formed in cell walls.

Ferulate Composition of Cell Walls.

Cell walls were incubated in aqueous NaOH near room temperature for 24 h to cleave and quantify ester-linked p-hydroxycinnamates in cell walls (Hartley, R. D.; Morrison III, W. H. *J. Sci. Food Agric.* 1991, 55, 365-375). Prior to artificial lignification, alkaline hydrolysis released 0.4 mg/g of p-coumarate, 8.4 mg/g of ferulate, and 4.7 mg/g of diferulates from nonlignified cell walls. Due to their extensive copolymerization into lignin by alkali-stable bonds (Grabber, J. H.; Ralph, J.; Hatfield, R. D. *J. Agric Food. Chem.* 2000, 48, 6106-6113), extremely low levels of alkali-labile ferulate and diferulates were released from xylans in cell walls lignified with only coniferyl alcohol (Table 1, shown in FIG. 4). Lignifying cell walls with coniferyl ferulate dramatically increased the amount of ferulate and, to a lesser degree, diferulate released by alkali. Lignifying cell walls with coniferyl ferulate also considerably increased the quantity of alkali-labile ferulate cross-coupled to coniferyl alcohol. As noted previously with ferulate xylan esters (Grabber, J. H.; Ralph, J.; Hatfield, R. D. *J. Agric. Food Chem.* 2002, 50, 6008-6016), 4-O-cross-coupled dimers predominated over 8-, and 5-dimers (data not shown). Assuming similar GC response factors for dimers, it appears that comparable amounts of alkali-releasable ferulate underwent homocoupling into diferulates vs heterocoupling into cross-coupled ferulate-coniferyl alcohol dimmers (Table 1, shown in FIG. 4).

Following lignification with coniferyl alcohol, alkali released 9% of the ferulates linked to cell wall xylans as ferulate monomers, diferulates, or cross-product dimers (Table 1, shown in FIG. 4). As the quantity of coniferyl-ferulate increased from 20 to 60% of the precursor mixture, the proportion of alkali-labile ferulates derived from cell wall xylans and lignin-incorporated coniferyl ferulate increased from 12 to 18%. Fortuitously, the source of these alkali-labile ferulates can be estimated from (Z)-ferulate levels. Nonlignified maize cell walls contained ~1.6 mg/g of alkali-labile (Z)-ferulates (as monomers or coupled as (E,Z)-diferulates) in addition to the predominant (E)-ferulate isomers (data not shown). Because only the (E)-isomer of coniferyl ferulate was used to lignify cell walls, reductions in the quantity of (Z)-ferulates released by alkali can be used as a general indicator of ferulate xylan ester incorporation into lignin via alkali stable bonds. In cell walls lignified with coniferyl alcohol, 92% of (Z)-ferulate was incorporated into lignin, which corresponds closely to the 91% overall incorporation of all ferulate monomers and dimers into lignin. As the proportion of coniferyl ferulate increased from 0 to 60%, the incorporation of (Z)-ferulate into lignin dropped from 92 to 60%. If this decline is typical, then cell wall xylans contributed roughly 45% of the ferulate monomers, diferulates, and cross-product dimers released by alkali from cell wall lignified with coniferyl ferulate. Thus, adding coniferyl ferulate with monolignols disrupted ferulate xylan ester incorporation into lignin in a manner analogous to that observed with a structurally related conjugate, sinapyl p-coumarate (Grabber, J. H.; Lu, F. *Planta* 2007, 226, 741-751). These calculations also indicate that about 90% of the ferulate moieties in coniferyl ferulate were oxidatively coupled to lignin oligomers or polymers. Therefore, ferulate moieties in coniferyl ferulate readily copolymerized into lignin and their addition significantly reduced ferulate xylan cross-linking of cell walls.

Delignification of Cell Walls.

Various treatments have been developed to delignify herbaceous or woody biomass for fermentative processes or pulp production (Dien, B. S.; Iten, L. B.; Skory, C. D. *Handbook of Industrial Biocatalysis*; CRC Press LLC: Boca Raton, Fla., 2005; pp 1-11; Shatalov, A. A.; Pereira, H. *Bioresour. Biotechnol.* 2005, 96, 865-872; Gratzl, J. S.; and Chen, C. L. *Lignin: Historical, Biological, and Materials PerspectiVes*; ACS Symposium Series; American Chemical Society: Washington, D.C., 2000; Vol. 742, pp 392-421). Because lignins containing ester inter-unit linkages should be readily cleaved by alkali, 0.5 M aqueous NaOH was used to study how the incorporation of coniferyl ferulate affects cell-wall delignification. A 30° C. treatment for 24 h was chosen to represent a mild alkaline pretreatment of biomass for ethanol fermentation (Dien, B. S.; Iten, L. B.; Skory, C. D. *Handbook of Industrial Biocatalysis*; CRC Press LLC: Boca Raton, Fla., 2005; pp 1-11). To represent harsher biomass pretreatments and pulping conditions, (Dien, B. S.; Iten, L. B.; Skory, C. D. *Handbook of Industrial Biocatalysis*; CRC Press LLC: Boca Raton, Fla., 2005; pp 1-11; Shatalov, A. A.; Pereira, H. *Bioresour. Biotechnol.* 2005, 96, 865-872; and Gratzl, J. S.; Chen, C. L. *Lignin: Historical, Biological, and Materials PerspectiVes*; ACS Symposium Series; American Chemical Society: Washington, D.C., 2000; Vol. 742, pp 392-421) refluxing at 100° C. and cooking at 160° C. for 2.5 h was used. Refluxing at 100° C. generally cleaves recalcitrant ester inter-unit linkages and fully solubilizes nonbound lignins, while cooking at 160° C. for 2.5 h with anthraquinone should solubilize additional lignin by cleaving ether inter-unit linkages. In these studies, NaOH concentrations, temperature, time, and anthraquinone levels were not optimized or meant to fully mimic potential commercial practices. The conditions were selected merely to illustrate how coniferyl ferulate incorporation into lignin affects the ease of cell-wall delignification by alkali.

Figures 5A, 5B:
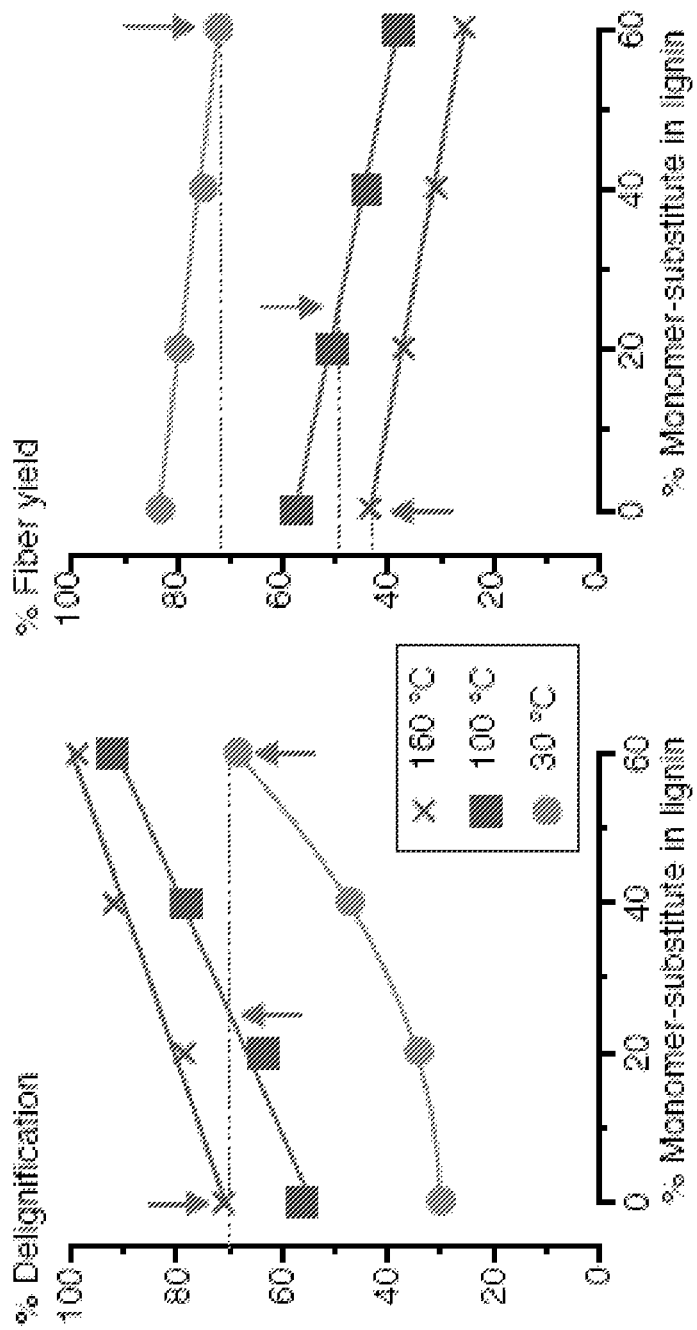
FIGS. 5A and 5B: Delignification (FIG. 5A) of alkali-soluble lignin and fiber yield (FIG. 5B) by aqueous 0.5 M NaOH at 30° C. (22 h), 100° C. (2.5 h), or 160° C. (1.5 h, with anthraquinone) from artificially lignified cell walls of maize prepared with 0 to 60% coniferyl ferulate. Bars indicate±SEM.

The proportion of lignin solubilized with aqueous 0.5 M NaOH increased with the severity of hydrolysis conditions and with the proportion of coniferyl ferulate used to form lignin (see FIGS. 5A and 5B). At 30° C., alkali-soluble lignin, as a proportion of cell-wall lignin increased quadratically from 32 to 66% as coniferyl ferulate increased from 0 to 60% of precursors. At higher temperatures, coniferyl ferulate additions linearly increased alkali-soluble lignin from 57 to 93% at 100° C., and from 69 to 99% at 160° C. While alkaline extraction of about 70% of lignin required heating at 160° C. for cell walls lignified with coniferyl alcohol, heating at 100° C. sufficed if coniferyl ferulate comprised about 30% of lignin precursors. Alternatively, coniferyl ferulate addition also permitted more extensive delignification of cell walls at normal 160° C. cooking temperatures. Because coniferyl ferulate reduced the amount of lignin formed in cell walls it had less effect on the total quantity of alkali-soluble lignin released particularly at 160° C. (see Table 2, shown in FIG. 6).

Incorporation of coniferyl ferulate into lignins dramatically improved the delignifcation of walls under both mild and severe pulping conditions (FIGS. 5A and 5B). Typical pulping conditions (160° C. with anthraquinone for 1.5 h) removed 70% of the lignin from "normal" walls lignified with coniferyl alcohol. The data in FIG. 5A indicate a similar degree of delignification can be obtained under refluxing conditions (100° C. for 2.5 h) if lignins are formed with ~25% coniferyl ferulate. A similar degree of delignification may be obtained under even milder conditions (30° C. for 20 h) if lignins are formed with 60% coniferyl ferulate (see dotted line and arrows in FIG. 5A). Up to 40% of the lignins in grasses are formed by a related conjugate (sinapyl p-coumarate), so similar levels of coniferyl ferulate incorporation are plausible. The arrows in FIG. 5B indicate the fiber yields at 70% delignification. Higher pulp yields can be anticipated because of the easier delignification. These results show that incorporating coniferyl ferulate into the lignin allows the lignin to be disassembled using much gentler conditions.

Figure 7:
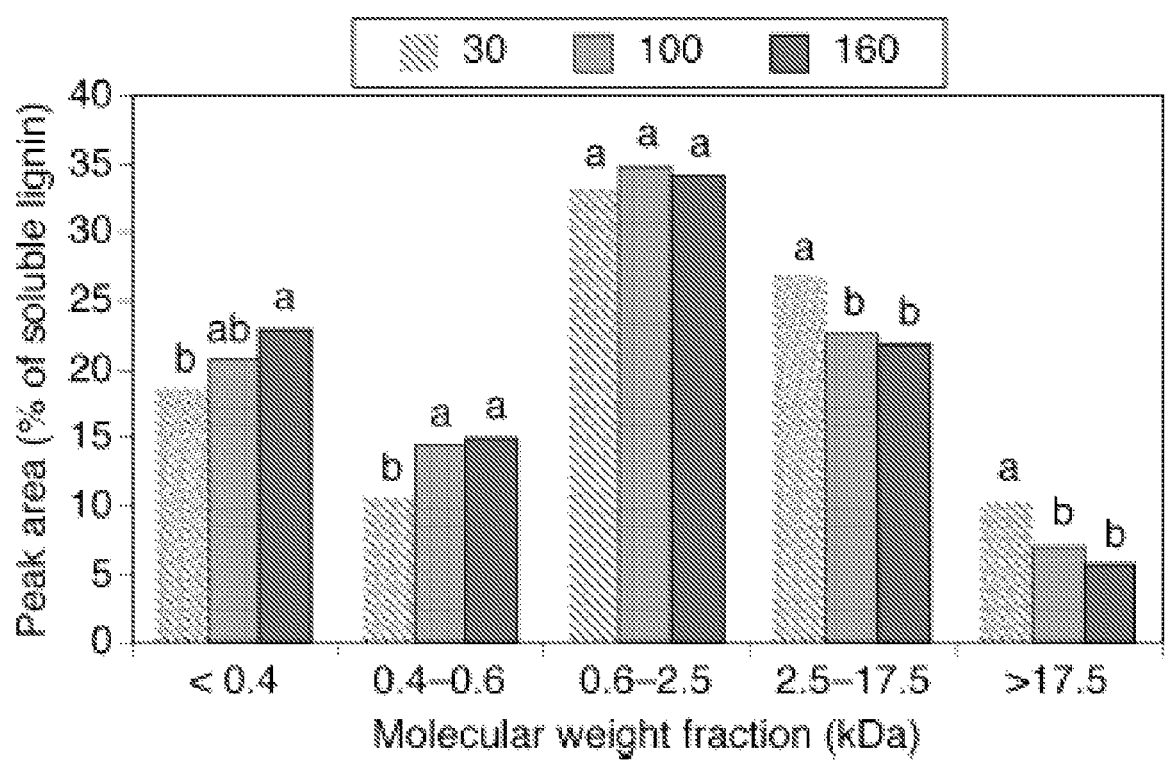
FIG. 7: Molecular weight distribution of alkali-soluble lignins released from maize cell walls by aqueous 0.5 M NaOH at 30, 100, or 160° C. Data are averaged over cell walls artificially lignified with 0-60% coniferyl ferulate. Means within a molecular weight group with unlike letters differ ($P<0.05$).
Figure 8:
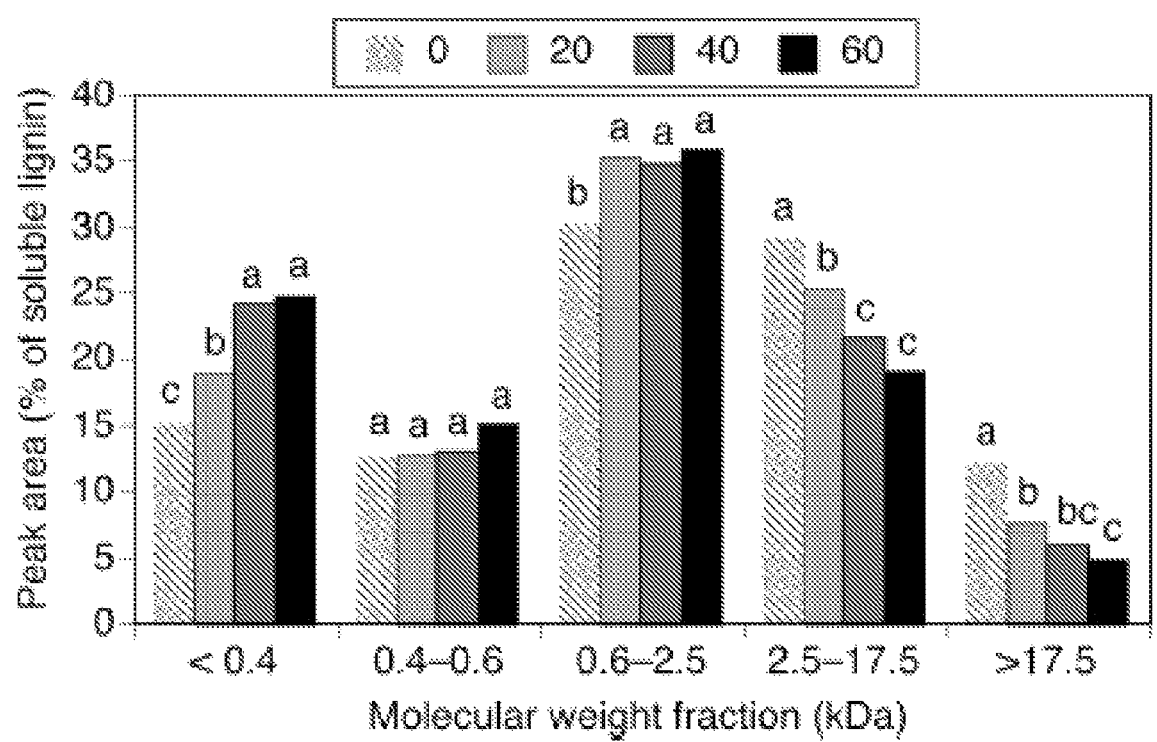
FIG. 8: Molecular weight distribution of alkali-soluble lignins from artificially lignified cell walls of maize prepared with 0-60% coniferyl ferulate. Data are averaged over 0.5 M NaOH treatments at 30, 100, and 160° C. Means within a molecular weight group with unlike letters differ ($P<0.05$).

Increased severity of delignification and greater proportions of coniferyl ferulate reduced the molecular weight of lignin released from cell walls. As the severity of delignification conditions increased, the proportion of oligomeric (2.5-17.5 kDa) and polymeric (>17.5 kDa) lignins declined, while the proportion of trimers and smaller fragments (<0.6 kDa) increased (FIG. 7). For all delignification treatments, incorporation of coniferyl ferulate into lignin mainly increased the proportion monomers and dimers (<0.4 kDa) and decreased the proportion of oligomeric (2.5-17.5 kDa) and polymeric (>17.5 kDa) lignins released from cell walls (FIG. 8). Consequently, incorporation of an ester interunit linkage into lignin via coniferyl ferulate enhanced alkaline depolymerization of lignin, leading to a greater release of lignin from cell walls. Conversely, ferulate's ability to act as an initiation site for lignin polymerization (Grabber, J. H.; Ralph, J.; Hatfield, R. D. *J. Agric. Food Chem.* 2002, 50, 6008-6016; Ralph, J.; Grabber, J. H.; Hatfield, R. D. *Carbohydr. Res.* 1995, 275, 167-178) could mean that continual coniferyl ferulate addition truncated polymerization to yield more numerous and smaller lignin chains than would be obtained with normal monolignols. In either case, cleavage of ester inter-unit linkages or a lower inherent size of polymers both contribute to enhanced solubilization of cell wall lignins formed with coniferyl ferulate.

Figure 9:
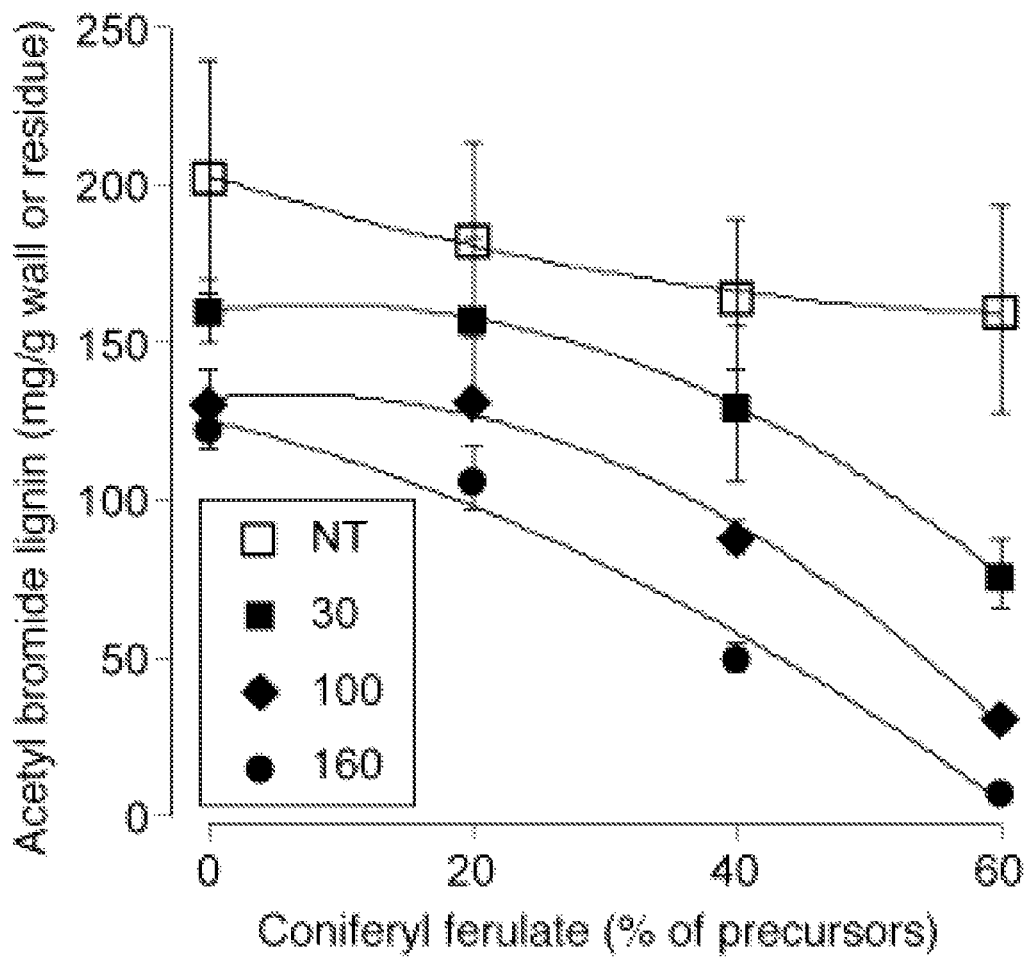
FIG. 9: Impact of forming lignins with 0-60% coniferyl ferulate on the lignin content of non-treated (NT) cell walls and of alkali-insoluble residues recovered following hydrolysis at 30, 100, or 160° C. Bars indicate±SEM.

Due to greater lignin extractability and lower intrinsic lignin levels, the lignin content of alkali-insoluble residue (AIR) at each temperature dropped dramatically as the proportion of coniferyl ferulate increased (FIG. 9). Thus, while a 160° C. alkaline hydrolysis of walls lignified with coniferyl alcohol yielded AIR with 123 mg/g of lignin, AIR with comparable lignin levels could be obtained at 100° C. with ~30% coniferyl ferulate. Alternatively, heating cell walls lignified with ~30% of coniferyl ferulate at 160° C. yields AIR with much lower lignin concentrations. As a result, incorporation of coniferyl ferulate into lignin enables pulping at lower temperatures or pulping at high temperature with reduced cooking time, and likely eliminating the need for bleaching.

Yields of alkali-soluble carbohydrate (ASC) increased and AIR decreased, as coniferyl ferulate comprised a greater proportion of lignin. (Table 2, shown in FIG. 6). The response of these fractions tended to be most pronounced at low to moderate levels of coniferyl ferulate addition and at higher hydrolysis temperatures. As hydrolysis temperatures increased to 160° C., the recovery of AIR from nonlignified cell walls and cell walls lignified with 40% of coniferyl ferulate leveled off near the cellulose content of cell walls (~250 mg/g) (Grabber, J. H.; Ralph, J.; Hatfield, R. D. *J. Agric. Food Chem.* 1998, 46, 2609-2614). Because coniferyl ferulate renders lignin more extractable by alkali, it would follow that pectin and hemicellulose extraction would improve as well. Indeed, lignin-degrading pretreatments are often used to improve the extractability of noncellulosic polysaccharides for analysis (Selvendran, R. R.; Stevens, B. J. H.; O'Neill, M. A. In *Biochemistry of Plant Cell Walls*; Brett, C. T., Hillman, J. R., Eds.; Cambridge University Press: Cambridge, 1985; pp 39-78.(41) Grabber, J. H.; Hatfield, R. D.; Ralph, J. *J. Agric. Food Chem.* 2003, 51, 4984-4989). Hence, at a given temperature, delignification of cell walls containing coniferyl ferulate yields AIR with less noncellulosic and, as mentioned above, less lignin contamination. Alternatively, coniferyl ferulate provides the option of delignifying cell walls under milder conditions to increase total fiber yields. For example, cell walls lignified with coniferyl alcohol yielded 497 mg/g of AIR at 160° C. compared to 749 mg/g of AIR at 30° C. for cell wall lignified with 40% coniferyl ferulate (Table 2, FIG. 6); both types of AIR contained similar amounts of lignin (~130 mg/g, FIG. 9).

Enzymatic Hydrolysis of Cell Walls and Alkali Insoluble Residues.

Figures 11A, 11B:
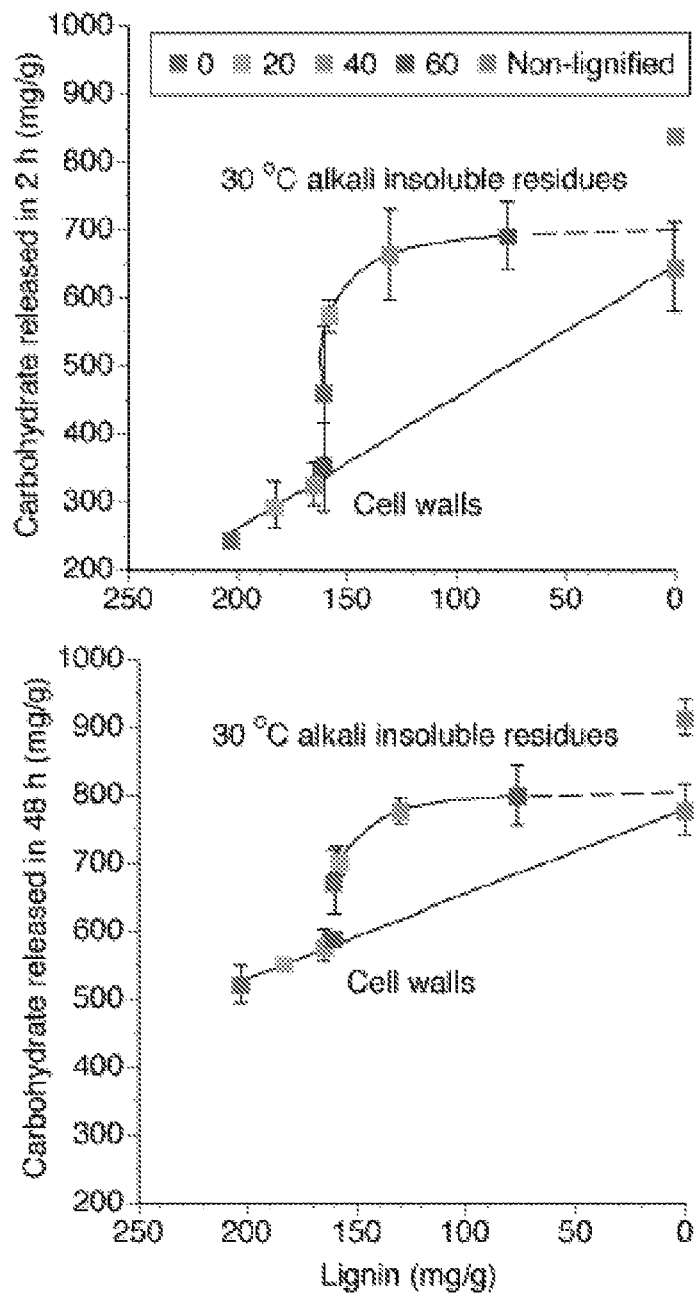
FIG. 11A: Relationship between lignin content and carbohydrate released after a two-hour (2 h) enzymatic hydrolysis of cell walls (lignified with 0-60% coniferyl ferulate or non-lignified) and their alkali-insoluble residues prepared with 0.5 M NaOH at 30° C. Bars indicate±SEM.
FIG. 11B: Relationship between lignin content and carbohydrate released after a forty-eight-hour (48 h) enzymatic hydrolysis of cell walls (lignified with 0-60% coniferyl ferulate or nonlignified) and their alkali-insoluble residues prepared with 0.5 M NaOH at 30° C. Bars indicate±SEM.

Cell walls and alkali-insoluble residues were incubated with high loadings of fibrolytic enzymes to assess whether coniferyl ferulate incorporation into lignin enhances the rate, and above all, the extent of structural polysaccharide hydrolysis. The release of all sugars (i.e., glucose, arabinose, xylose, galactose, uronosyls) responded similarly to coniferyl ferulate incorporation into lignin; therefore, only total carbohydrate yields are reported and discussed below. Incorporation of coniferyl ferulate into lignin improved carbohydrate yields from both cell walls and AIR recovered following treatment with aqueous NaOH at 30° C. (Table 3, shown in FIG. 10). Prior to alkaline pretreatment, yields of carbohydrates from artificially lignified and nonlignified cell walls linearly increased as lignin content declined after both 2 and 48 h of enzymatic hydrolysis (FIGS. 11A and 11B, respectively). Thus, coniferyl ferulate enhanced carbohydrate yields primarily by reducing the lignin content of cell walls. Even so, reduced cross-linking of lignin to feruloylated xylans with coniferyl ferulate additions could also play a role in enhancing cell wall hydrolysis (Grabber, J. H.; Ralph, J.; Hatfield, R. D. *J. Agric. Food Chem.* 1998, 46, 2609-2614).

Pretreatment with NaOH dramatically improved the enzymatic hydrolysis of carbohydrates from AIR derived from all types of lignified cell walls (Table 3, shown in FIG. 10). The dramatic degradability response of grass cell walls to alkaline pretreatments has been mainly attributed to cleavage of cross-links between lignin and feruloylated xylans and to lignin extraction (Fahey, G. C., Jr.; Bourquin, L. D.; Titgemeyer, E. C.; Atwell, D. G. In *Forage Cell Wall Structure and Digestibility*; Jung, H. G., Buxton, D. R., Hatfield, R. D., Ralph, J., Eds.; Am. Soc. Agronomy: Madison, Wis., 1993; pp 715-766). Coniferyl ferulate improved lignin extractability and carbohydrate yields from AIR, but yields quickly plateaued even as lignin levels continued to decline (see FIGS. 11A and 11B). Indeed, after both 2 and 48 h of enzymatic hydrolysis, maximal carbohydrate yields from lignified AIR were >100 mg/g lower than nonlignified AIR, indicating lignin content per se was not the only factor limiting cell wall hydrolysis.

On a cell wall basis, hydrolytic enzymes released a fairly constant proportion of carbohydrate from AIR derived from nonlignified and lignified cell walls (Table 3, shown in FIG. 10). If ASC are included, then total fermentable carbohydrate yields following alkaline pretreatment were greatest from nonlignified cell walls, intermediate from cell walls lignified with coniferyl ferulate, and lowest from cell walls lignified with coniferyl alcohol. Thus, the benefits of alkaline pretreatment and incorporation of alkali-labile coniferyl ferulate into grass lignins will only be fully realized if noncellulosic ASC are recovered and utilized for fermentation. This also indicates shifts in lignin alkaline solubility mainly alters the proportion of nondegradable carbohydrate versus ASC in cell walls without markedly changing the size of the degradable AIR fraction in cell walls. While not examined here, coniferyl ferulate incorporation into lignin could also reduce biomass conversion costs if lower enzyme loadings could be used for saccharification.

Based on these Examples, incorporation of coniferyl ferulate into graminaceous feedstocks reduces lignifications and permits more efficient delignification and enzymatic hydrolysis of cell walls. This in turn reduces inputs for energy, pressure vessel construction, and bleaching during papermaking, and lessens pretreatment and enzyme costs associated with biomass conversion. Comparable or greater benefits are anticipated for hardwoods, softwoods, and herbaceous dicots that have lower inherent lignin extractability.

In preliminary studies, adding sinapyl ferulate with coniferyl and sinapyl alcohols had comparable effects on lignin formation, lignin extractability, and cell wall degradability. Therefore, genetic engineering of plants to incorporate coniferyl ferulate into guaiacyl lignins in softwoods or coniferyl and sinapyl ferulates into mixed syringyl-guaiacyl-type lignins in hardwoods and herbaceous plants will greatly enhance the utilization of plant cell walls.

REFERENCES

The following references are incorporated herein by reference:

(1) Ralph, J.; Lundquist, K.; Brunow, G.; Lu, F.; Kim, H.; Schatz, P. F.; Marita, J. M.; Hatfield, R. D.; Ralph, S. A.; Christensen, J. H.; Boerjan, W. *Phytochem. ReV.* 2004, 3, 29-60.
(2) Ralph, J.; Hatfield, R. D.; Quideau, S.; Helm, R. F.; Grabber, J. H.; Jung, H.-J. G. *J. Am. Chem. Soc.* 1994, 116, 9448-9456.
(3) Grabber, J. H.; Quideau, S.; Ralph, J. *Phytochemistry* 1996, 43, 1189-1194.
(4) Lu, F.; Ralph, J. 13th International Symposium on Wood, Fiber, and Pulping Chemistry, Auckland, New Zealand, May 16-19, 2005, APPITA: Auckland, New Zealand, 2005; pp 233-237.
(5) Hatfield, R. D.; Wilson, J. R.; Mertens, D. R. *J. Sci. Food Agric.* 1999, 79, 891-899.
(6) Oosterveld, A.; Grabber, J. H.; Beldman, G.; Ralph, J.; Voragen, A. G. *J. Carbohydr. Res.* 1997, 300, 179-181.
(7) Grabber, J. H.; Hatfield, R. D.; Ralph, J.; Zon, J.; Amrhein, N. *Phytochemistry* 1995, 40, 1077-1082.
(8) Grabber, J. H.; Ralph, J.; Hatfield, R. D. *J. Agric Food. Chem.* 2000, 48, 6106-6113.
(9) Grabber, J. H.; Ralph, J.; Hatfield, R. D. *J. Agric. Food Chem.* 2002, 50, 6008-6016.
(10) Ralph, J.; Helm, R. F.; Quideau, S.; Hatfield, R. D. *J. Chem. Soc., Perkin Trans. 1* 1992, 2961-2969.
(11) Fahey, G. C., Jr.; Bourquin, L. D.; Titgemeyer, E. C.; Atwell, D. G. In *Forage Cell Wall Structure and Digestibility*; Jung, H. G., Buxton, D. R., Hatfield, R. D., Ralph, J., Eds.; Am. Soc. Agronomy: Madison, Wis., 1993; pp 715-766.
(12) Paula, V. F.; Barbosa, L. C. A.; Howarth, O. W.; Demuner, A. J.; Cass, Q. B.; Vieira, I. J. C. *Tetrahedron* 1995, 51, 12453-12462.
(13) Seca, A. M. L.; Silva, A. M. S.; Silvestre, A. J. D.; Cavaleiro, J. A. S.; Domingues, F. M. J.; Pascoal-Neto, C. *Phytochemistry* 2001, 56, 759-767.
(14) Hsiao, J. J.; Chiang, H. C. *Phytochemistry* 1995, 39, 899-902.
(15) Li, S. L.; Lin, G.; Tam, Y. K. *Planta Med.* 2005, 72, 278-280.
(16) Baucher, M.; Halpin, C.; Petit-Conil, M.; Boerjan, W. *Crit. ReV. Biochem. Mol. Biol.* 2003, 38, 305-350.
(17) Dien, B. S.; Jung, H. J. G.; Vogel, K. P.; Casler, M. D.; Lamb, J. F. S.; Iten, L.; Mitchell, R. B.; Sarath, G. *Biomass Bioenergy* 2006, 30, 880-891.
(18) Murnen, H. K.; Balan, V.; Chundawat, S. P. S.; Bals, B.; Sousa, L. D.; Dale, B. E. *Biotechnol. Prog.* 2007, 23, 846-850.
(19) Grabber, J. H. *Crop Sci.* 2005, 45, 820-831.
(20) Grabber, J. H.; Ralph, J.; Hatfield, R. D.; Quideau, S.; Kuster, T.; Pell, A. N. *J. Agric. Food Chem.* 1996, 44, 1453-1459.
(21) Grabber, J. H.; Lu, F. *Planta* 2007, 226, 741-751.
(22) Lu, F.; Ralph, J. *J. Agric. Food Chem.* 1998, 46, 2911-2913.
(23) Lu, F.; Ralph, J. *J. Agric. Food Chem.* 1998, 46, 1794-1796.
(24) Kubes, G. J.; B. I., F.; MacLeod, J. M.; Bolker, H. I. *Wood Sci. Technol.* 1980, 14, 207-228.
(25) Majcherczyk, A.; Huttermann, A. *J. Chromatogr., A* 1997, 764, 183-191.
(26) Hatfield, R. D.; Grabber, J. H.; Ralph, J.; Brei, K. *J. Agric. Food Chem.* 1999, 47, 628-632.
(27) Hatfield, R. D.; Jung, H. G.; Ralph, J.; Buxton, D. R.; Weimer, P. J. *J. Sci. Food Agric.* 1994, 65, 51-58.
(28) Kim, H.; Ralph, J.; Akiyama, T., *Bioenerg. Res.* 2008, 1, 56-66.
(29) Grabber, J. H.; Ralph, J.; Hatfield, R. D. *J. Agric. Food Chem.* 1998, 46, 2609-2614.
(30) Blumenkrantz, N.; Asboe-Hansen, G. *Anal. Biochem.* 1973, 54, 484-489.
(31) Shea, E. M.; Hatfield, R. D. *J. Agric. Food Chem.* 1993, 41, 380-387.
(32) Hatfield, R. D.; Weimer, P. J. *J. Sci. Food Agric.* 1995, 69, 185-196.
(33) SAS, PC Windows Version 9.1.3; SAS Institute Inc.: Cary, N.C., 2003.
(34) Fukushima, R. S.; Hatfield, R. D. *J. Agric. Food Chem.* 2004, 52, 3713-3720.
(35) Hartley, R. D.; Morrison III, W. H. *J. Sci. Food Agric.* 1991, 55, 365-375.
(36) Dien, B. S.; Iten, L. B.; Skory, C. D. *Handbook of Industrial Biocatalysis*; CRC Press LLC: Boca Raton, Fla., 2005; pp 1-11.
(37) Shatalov, A. A.; Pereira, H. *Bioresour. Biotechnol.* 2005, 96, 865-872.
(38) Gratzl, J. S.; Chen, C. L. *Lignin: Historical, Biological, and Materials PerspectiVes*; ACS Symposium Series; American Chemical Society: Washington, D.C., 2000; Vol. 742, pp 392-421.
(39) Ralph, J.; Grabber, J. H.; Hatfield, R. D. *Carbohydr. Res.* 1995, 275, 167-178.
(40) Selvendran, R. R.; Stevens, B. J. H.; O'Neill, M. A. In *Biochemistry of Plant Cell Walls*; Brett, C. T., Hillman, J. R., Eds.; Cambridge University Press: Cambridge, 1985; pp 39-78.
(41) Grabber, J. H.; Hatfield, R. D.; Ralph, J. *J. Agric. Food Chem.* 2003, 51, 4984-4989.
(42) Ralph, S. A.; Landucci, L. L.; Ralph, J. http://ars.usda.gov/Services/docs.htm?docid)10429, 2005. BM800528F

What is claimed is:

1. An isolated lignified plant cell wall comprising an isolated plant cell wall that includes lignin, wherein the lignin includes a ferulate residue incorporated therein, wherein the ferulate residue is a ferulate-monolignol ester conjugate, wherein the ferulate-monolignol ester conjugate comprises a monolignol moiety esterified to a ferulate moiety via a γ-carbon on the monolignol moiety, wherein both the monolignol moiety and the ferulate moiety are independently incorporated within the lignin.

2. The isolated lignified plant cell wall of claim 1, wherein the ferulate residue is selected from a monomer conjugate group consisting of coniferyl ferulate and sinapyl ferulate.

3. The isolated lignified plant cell wall of claim 1, derived from maize.

4. The isolated lignified plant cell wall of claim 1, derived from a tree.

5. The isolated lignified plant cell wall of claim 4, derived from a tree of the family Myrtaceae, Salicaceae, or a hybrid thereof.

6. The isolated lignified plant cell wall of claim 5, derived from a tree of a genus selected from the group consisting of *Salix, Eucalyptus, Corymbia*, and *Angophora*, or a hybrid thereof.

7. The isolated lignified plant cell wall of claim 1, derived from a eucalyptus tree, a poplar tree, a willow tree, or a hybrid thereof.

8. The isolated lignified plant cell wall of any one of claims 1-7, wherein the ferulate residue is derived from coniferyl ferulate.

9. The isolated lignified plant cell wall of any one of claims 1-7, wherein the ferulate residue is derived from sinapyl ferulate.

10. A method of manufacturing modified lignin, the method comprising:
   conducting a lignin-producing polymerization reaction in a cell wall in the presence of at least one polymerizable monomer comprising a ferulate-monolignol ester conjugate, wherein the ferulate-monolignol ester conjugate comprises a monolignol moiety esterified to a ferulate moiety via a γ-carbon on the monolignol moiety,
   wherein at least one of the polymerizable monomers is incorporated into the resulting lignin wherein both the monolignol moiety and the ferulate moiety are independently incorporated within the lignin.

11. The method of claim 10, wherein the polymerizable monomer is selected from the group consisting of coniferyl ferulate and sinapyl ferulate.

12. The method of claim 10 or claim 11, wherein from about 10% by wt to about 60% by wt of the polymerizable monomers are reacted in the polymerization reaction.

13. The method of claim 10 or claim 11, wherein the polymerization reaction is conducted in vitro.

14. The method of claim 13, wherein the polymerization reaction comprises isolating a cell wall from a plant cell suspension and lignifying the cell wall in the presence of the polymerizable monomer.

15. The method of claim 14, wherein the plant cell suspension is isolated from maize.

16. The method of claim 14, wherein the plant cell suspension is isolated from a tree of the family Myrtaceae, Salicaceae, or a hybrid thereof.

17. The method of claim 14, wherein the plant cell suspension is isolated from a tree of a genus selected from the group consisting of Eucalyptus, Corymbia, and Angophora, or a hybrid thereof.

18. The method of claim 14, wherein the plant cell suspension is isolated from a eucalyptus tree, a poplar tree, a willow tree, or a hybrid thereof.

19. The method of claim 10 or claim 11, wherein the polymerization reaction is conducted in vivo.

20. A modified lignin produced by a method comprising:
   conducting a lignin-producing polymerization reaction in a cell wall in the presence of at least one polymerizable monomer comprising a ferulate-monolignol ester conjugate, wherein the ferulate-monolignol ester conjugate comprises a monolignol moiety esterified to a ferulate moiety via a γ-carbon on the monolignol moiety,
   wherein at least one of the polymerizable monomers is incorporated into the resulting lignin wherein both the monolignol moiety and the ferulate moiety are independently incorporated within the lignin.

21. The modified lignin of claim 20 wherein the polymerizable monomer is selected from the group consisting of coniferyl ferulate and sinapyl ferulate.

22. The method of claim 20, wherein the polymerization reaction is conducted in vivo.

23. The method of claim 20, wherein the polymerization reaction is conducted in vitro.

24. The method of claim 23, wherein the polymerization reaction comprises isolating a cell wall from a plant cell suspension and lignifying the cell wall in the presence of the polymerizable monomer.

* * * * *